US012649008B2

(12) United States Patent
Sutcliffe

(10) Patent No.: US 12,649,008 B2
(45) Date of Patent: Jun. 9, 2026

(54) PEPTIDE RECEPTOR RADIONUCLIDE THERAPY

(71) Applicant: The Regents of the University of California, Oakland, CA (US)

(72) Inventor: Julie L. Sutcliffe, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 494 days.

(21) Appl. No.: 18/038,851

(22) PCT Filed: Dec. 3, 2021

(86) PCT No.: PCT/US2021/061886

§ 371 (c)(1),
(2) Date: May 25, 2023

(87) PCT Pub. No.: WO2022/120226

PCT Pub. Date: Jun. 9, 2022

(65) Prior Publication Data

US 2024/0131206 A1 Apr. 25, 2024

Related U.S. Application Data

(60) Provisional application No. 63/121,762, filed on Dec. 4, 2020.

(51) Int. Cl.

| | |
|---|---|
| ***A61K 51/08*** | (2006.01) |
| ***A61K 38/16*** | (2006.01) |
| ***A61K 47/60*** | (2017.01) |
| ***A61P 35/00*** | (2006.01) |

(52) U.S. Cl.

CPC ............ *A61K 51/088* (2013.01); *A61K 38/16* (2013.01); *A61K 47/60* (2017.08); *A61P 35/00* (2018.01)

(58) Field of Classification Search

CPC .............................. A61K 51/088; A61K 38/16

See application file for complete search history.

(56) References Cited

U.S. PATENT DOCUMENTS

| | | | |
|---|---|---|---|
| 11,185,601 | B2 | 11/2021 | Tang et al. |
| 11,485,758 | B2 | 11/2022 | Hausner et al. |
| 11,591,369 | B2 | 2/2023 | Tang et al. |
| 12,023,391 | B2 | 7/2024 | Tang et al. |
| 2012/0015899 | A1 | 1/2012 | Lomonossoff et al. |
| 2020/0283532 | A1 | 9/2020 | Marshall et al. |
| 2020/0306391 | A1 | 10/2020 | Ray et al. |

FOREIGN PATENT DOCUMENTS

| | | |
|---|---|---|
| WO | 2015/160770 | 10/2015 |
| WO | 2018/098390 | 5/2018 |
| WO | 2020/051549 | 3/2020 |
| WO | 2021/226432 | 11/2021 |

OTHER PUBLICATIONS

Carrillo, C. et al. Polyprotein [Foot-and-mouth disease virus O]. GenBank: AAT01760.1 NCBI entry (online) National Center for Biotechnology Information, Apr. 28, 2005 [retrieved on Mar. 7, 2022] 3 pages.

Hausner et al. "Evaluation of [64Cu]Cu-DOTA and [64Cu]Cu-CB-TE2A Chelates for Targeted Positron Emission Tomography with an avB6-Specific Peptide" Mol Imaging. Mar. 2009-Apr; 8(2):111-121.

Hausner et al. "The Effects of an Albumin Binding Moiety on the Targeting and Pharmacokinetics of an Integrin alphavbeta6-Selective Peptide Labeled with Aluminum [(18)F]Fluoride", Mol Imaging Biol 22, 1543-1552 (2020).

Hausner et al. "Use of a peptide derived from foot-and-mouth disease virus for the noninvasive imaging of human cancer: Generation and evaluation of 4-[18F]fluorobenzoyl A20FMDV2 for in vivo imaging of integrin alpha(v)beta(6) expression with positron emission tomography" Cancer Res. 2007; 67: 7833-40.

Hausner et al., "In vitro and in vivo evaluation of the effects of aluminum [18F]fluoride radiolabeling on an integrin avB6- specific peptide" Nuclear medicine and biology. 2014; 41: 43-50.

Hausner SH, Bauer N, Hu LY, Knight LM, Sutcliffe JL. The Effect of Bi-Terminal PEGylation of an Integrin avß6- Targeted 18F Peptide on Pharmacokinetics and Tumor Uptake. J Nucl Med. May 2015;56(5):784-90. doi: 10.2967/jnumed. 114.150680. Epub Mar. 26, 2015. PMID: 25814519; PMCID: PMC4559355.

Hausner SH, Bold RJ, Cheuy LY, Chew HK, Daly ME, Davis RA, Foster CC, Kim EJ, Sutcliffe JL. Preclinical Development and First-in-Human Imaging of the Integrin avB6 with [18F]avB6-Binding Peptide in Metastatic Carcinoma. Clin Cancer Res. Feb. 15, 2019;25(4):1206-1215. doi: 10.1158/1078-0432.CCR-18-2665. Epub Nov. 6, 2018. PMID: 30401687; PMCID: PMC6377828.

Hu et al., "Characterization and Evaluation of 64Cu-Labeled A20FMDV2 Conjugates for Imaging the Integrin avB6", Mol Imaging Biol. 2014; 16: 567-77.

International Search Report and Written Opinion, International Patent Application No. PCT/US2021/061886, dated Mar. 25, 2022, 9 pages.

EP Search Report, EP Patent Application No. 21901568.2, dated Feb. 18, 2026, 8 pages.

Ui Takashi et al: "Development and characterization of a 68Ga-labeled A20FMDV2 peptide probe for the PET imaging of [alpha]v[beta]6 integrin-positive pancreatic ductal adenocarcinoma", Bioorganic & Medicinal Chemistry, Elsevier, Amsterdam, NL, vol. 28, No. 1, Nov. 9, 2019 (Nov. 9, 2019), 6 pages.

*Primary Examiner* — James W Rogers

(74) *Attorney, Agent, or Firm* — Casimir Jones, S.C.; J. Mitchell Jones

(57) ABSTRACT

The present disclosure provides methods and related compositions that incorporate a molecularly targeted approach via the integrin subtype $\alpha_v\beta_6$ using Peptide Receptor Radionuclide Therapy (PRRT) and a theranostic approach.

22 Claims, 10 Drawing Sheets

Specification includes a Sequence Listing.

FIG. 1A
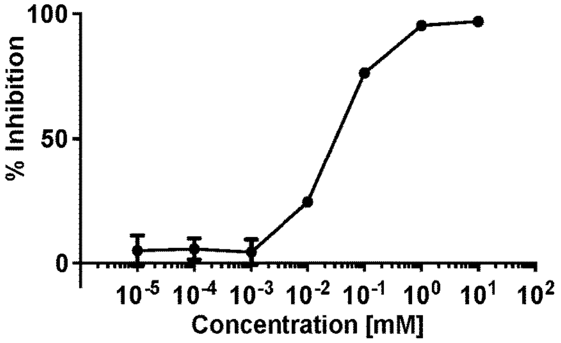
FIG. 1B
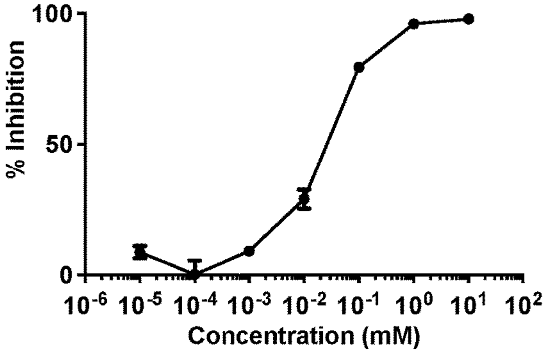
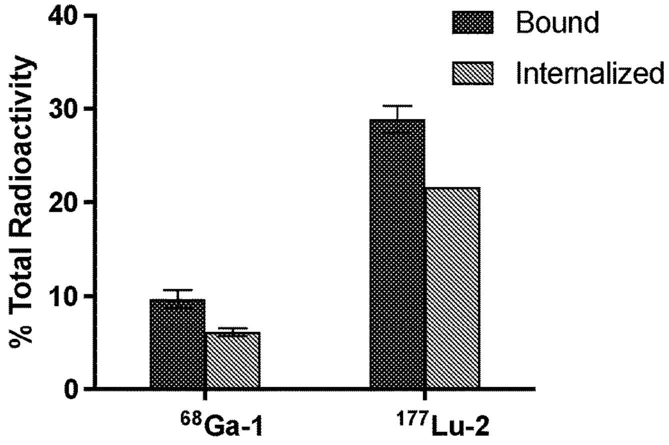
FIG. 1C
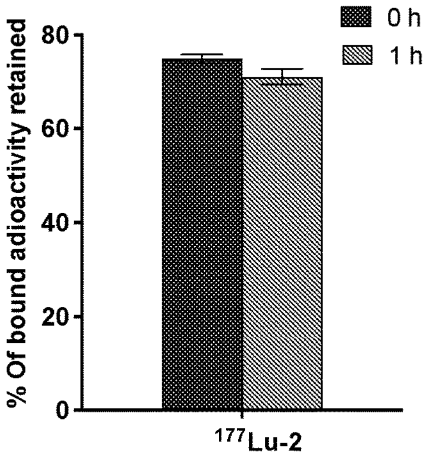
FIG. 1D

FIG. 8A
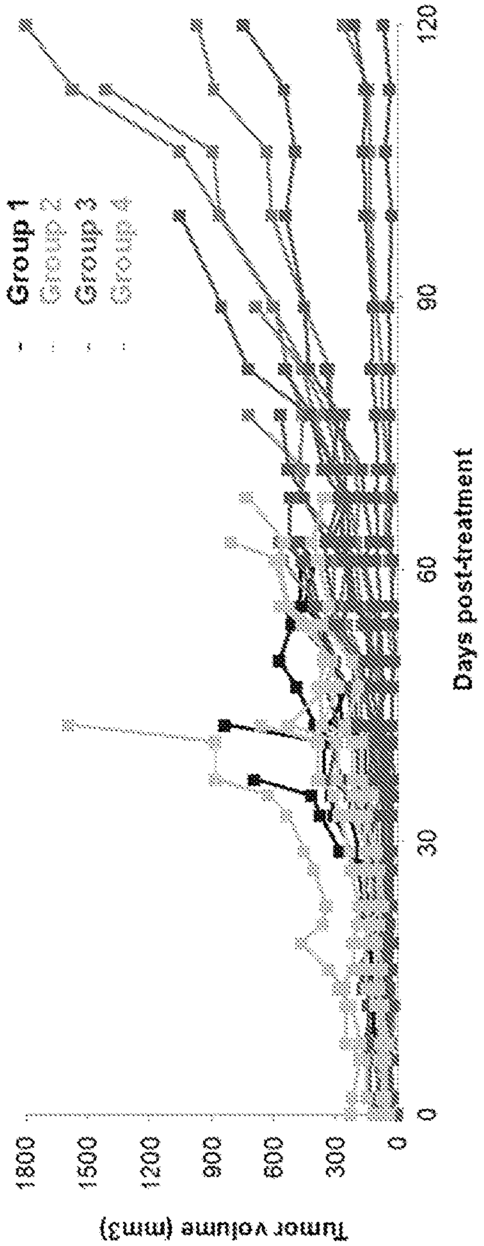
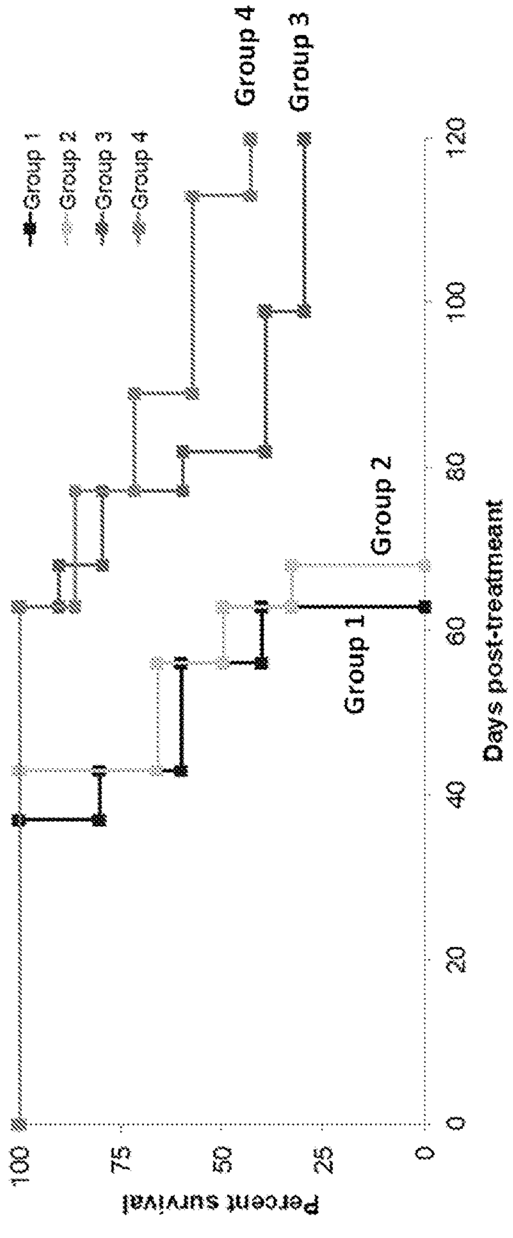
FIG. 8B

Peptide 1

Peptide 2

SEQUENCE LISTING

```
<160> NUMBER OF SEQ ID NOS: 7

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Asn Gly Val Pro Asn Leu Arg Gly Asp Leu Gln Val Leu Gly Gln
1               5                   10                  15

Arg Val Gly Arg Thr
            20


<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Leu or Ile
```

<400> SEQUENCE: 2

Arg Gly Asp Leu Xaa Xaa Xaa
1 5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Arg or Lys
<220> FEATURE:
<221> NAME/KEY: MOD_RES
<222> LOCATION: (4)..(4)
<223> OTHER INFORMATION: Ala or Gly

<400> SEQUENCE: 3

Gln Xaa Val Xaa Arg Thr
1 5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Gln Arg Val Gly Arg Thr
1 5

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Arg Gly Asp Leu Gln Val Leu Gly Gln Arg Val Gly Arg Thr
1 5 10

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Gly Asn Gly Val Pro Asn Leu Arg Gly Asp Leu Gln Val Leu Gly Gln
1 5 10 15

Arg Val Gly Arg Thr
20

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 7

Gly Asn Gly Val Pro Asn Leu Arg Gly Asp Leu Gln Val Leu Gly Gln
1               5                   10                  15

Arg Val Gly Arg Thr
            20
```

PEPTIDE RECEPTOR RADIONUCLIDE THERAPY

CROSS-REFERENCE TO RELATED APPLICATIONS

This application claims priority to U.S. Provisional Application No. 63/121,762, filed Dec. 4, 2020, the disclosure of which is herein incorporated by reference in its entirety for all purposes.

BACKGROUND

Cancers continue to be in need of new and more effective therapeutics. Particularly, some cancers and subsets within those cancer types are recalcitrant to current approaches. For example, the incidence of pancreatic ductal adenocarcinoma (PDAC) continues to increase with an estimated 47,000 people diagnosed in the United States in 2018. Unfortunately, PDAC remains the most lethal cancer with 98% of people ultimately succumbing to the disease. Despite exhaustive testing and some encouraging advances in first- and second-line treatment, only one chemotherapy (gemcitabine) has been found to have any benefit in this disease. However, the clinical response rate remains less than 10% with life prolongation a mere 6 weeks on average. The lack of clinical options for pancreatic cancer coupled with the dismal outcome demonstrate a clear unmet need for investigation into new therapies.

BRIEF SUMMARY

In one aspect, the present disclosure provides a method of treating an $\alpha_v\beta_6$ integrin-related cancer comprising administering a dose of a therapeutic conjugate of Formula I to a subject in need of treatment (Formula I)

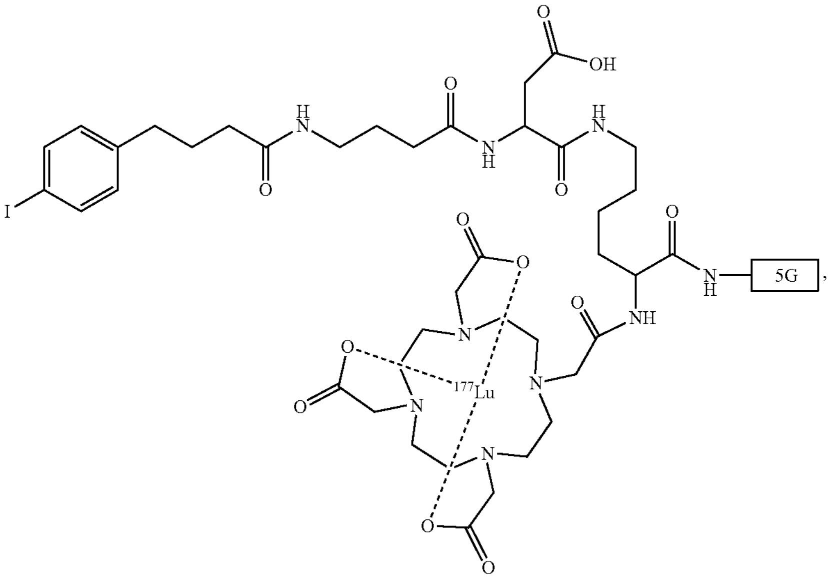

, wherein 5G is a PEGylated peptide having the amino acid sequence GNGVPNLRGDLQVLGQRVGRT and comprising a first PEG moiety at the N-terminus of the peptide and a second PEG moiety at the C-terminus of the peptide, and wherein the dose of the therapeutic conjugate contains between about 25 mCi and about 200 mCi radioactivity.

In a related aspect, the present disclosure provides a therapeutic conjugate for use in a method for treating an $\alpha_v\beta_6$ integrin-related cancer, the method comprising administering a dose of the therapeutic conjugate to a subject in need of treatment, wherein the therapeutic conjugate comprises Formula I (Formula I)

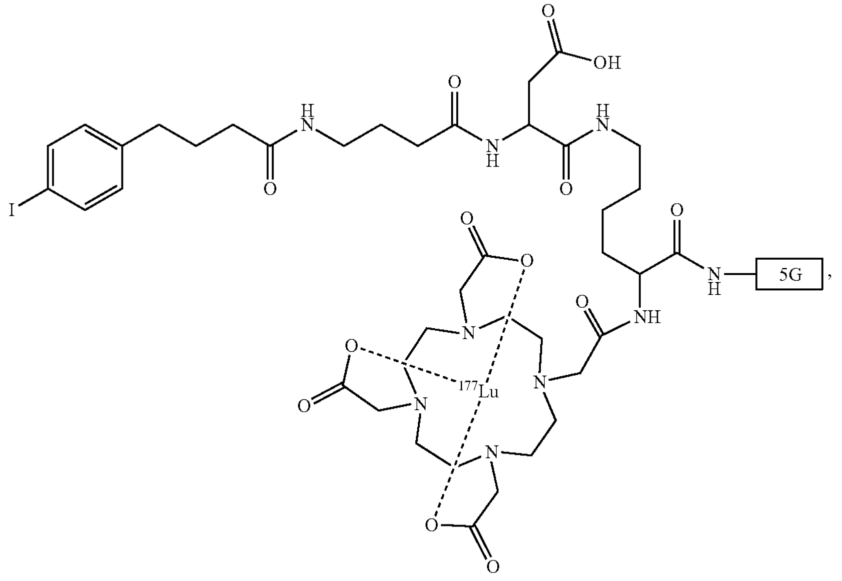

wherein 5G is a PEGylated peptide having the amino acid sequence GNGVPNLRGDLQVLGQRVGRT and comprising a first PEG moiety at the N-terminus of the peptide and a second PEG moiety at the C-terminus of the peptide, and wherein the dose of the therapeutic conjugate contains between about 25 mCi and about 200 mCi radioactivity.

In some embodiments, the first PEG moiety and the second PEG moiety are independently selected from the group consisting of PEG11, PEG12 (PEG 800), PEG28 (PEG 1500), and $(PEG28)_2$ (PEG 1500×2). In some embodiments, the first PEG moiety and the second PEG moiety are the same. In particular embodiments, the first PEG moiety and the second PEG moiety each comprises PEG28 (PEG 1500).

In some embodiments, the amount of radioactivity in the dose is 25 mCi, 50 mCi, 100 mCi, 150 mCi, or 200 mCi. In some embodiments, the method further comprises administering one, two, or three additional dose(s) of the therapeutic conjugate to the subject. In some embodiments, the dose includes no more than about 500 μg, about 400 μg, about 300 μg, about 200 μg, or about 100 μg of the peptide. In particular embodiments, the dose includes no more than about 100 μg of the peptide. In those embodiments where multiple doses of the therapeutic conjugate are administered to the subject, each dose can contain the same or a different amount of radioactivity and/or the same or a different amount of the peptide.

In some embodiments, the $\alpha_v\beta_6$ integrin-related cancer is pancreatic cancer, breast cancer, colorectal cancer, lung cancer, ovarian cancer, cervical cancer, oral squamous cell carcinoma, skin squamous cell carcinoma, stomach cancer, or endometrial cancer. In certain embodiments, the pancreatic cancer is locally advanced or metastatic pancreatic cancer; locally advanced, unresectable or metastatic pancreatic adenocarcinoma; or pancreatic ductal adenocarcinoma (PDAC).

In some embodiments, the $\alpha_v\beta_6$ integrin-related cancer comprises a primary lesion and a metastatic lesion. In certain embodiments, the $\alpha_v\beta_6$ integrin-related cancer comprises a lesion in an adrenal gland, bone, brain, liver, lung or any combination thereof.

In some embodiments, the subject receives a standard of care treatment prior to the administering of the dose of the therapeutic conjugate. In some embodiments, the subject receives a standard of care treatment subsequent to the administering of the dose of the therapeutic conjugate. In some embodiments, the subject receives a standard of care treatment prior to and subsequent to the administering of the dose of the therapeutic conjugate. In some embodiments, the standard of care treatment comprises one or more of surgery, radiation therapy, chemotherapy, chemoradiation therapy and targeted therapy. In particular embodiments, the standard of care treatment comprises FOLFIRINOX (leucovorin calcium (folinic acid), fluorouracil, irinotecan hydrochloride and oxaliplatin), gemcitabine, abraxane, irinotecan, or a combination thereof.

In some embodiments, the method further comprises scanning the body of the subject or a portion thereof after administering the therapeutic conjugate. In certain embodiments, the scanning comprises positron emission tomography (PET), computed tomography (CT) scanning, or single photon emission computerized tomography (SPECT).

In some embodiments, the method further comprises administering a diagnostic conjugate prior to the administration of the therapeutic conjugate, wherein the diagnostic conjugate comprises an RGD peptide and a second radionuclide, such as a different radionuclide suitable for imaging. In certain embodiments, the second radionuclide is $^{68}Ga$. In certain embodiments, the diagnostic conjugate is administered in a dose that contains up to about 5 mCi (e.g., greater than about 0.01 mCi to about 5 mCi) radioactivity.

In some embodiments, the method further comprises scanning the body of the subject or a portion thereof after administering the diagnostic conjugate. In certain embodiments, the scanning comprises positron emission tomography (PET), computed tomography (CT) scanning, or single photon emission computerized tomography (SPECT).

In some embodiments, the therapeutic conjugate is administered within 5 weeks after the administration of the diagnostic conjugate.

In particular embodiments, the diagnostic conjugate comprises Formula II (Formula II)

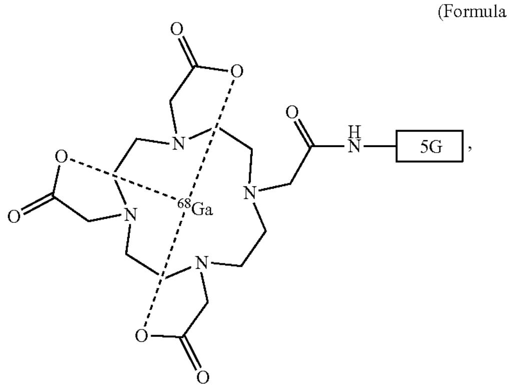

and wherein 5G is a PEGylated peptide having the amino acid sequence GNGVPNLRGDLQVLGQRVGRT and comprising a first PEG moiety at the N-terminus of the peptide and a second PEG moiety at the C-terminus of the peptide.

In some embodiments, the first PEG moiety and the second PEG moiety in the diagnostic conjugate are independently selected from the group consisting of PEG11, PEG12 (PEG 800), PEG28 (PEG 1500), and $(PEG28)_2$ (PEG 1500×2). In some embodiments, the first PEG moiety and the second PEG moiety are the same. In particular embodiments, the first PEG moiety and the second PEG moiety each comprises PEG28 (PEG 1500).

In some embodiments, the method further comprises administering a solution of amino acids to the subject. In certain embodiments, the solution is administered prior to and concurrent with the administration of the therapeutic conjugate.

In some embodiments, the therapeutic conjugate is administered to the subject by infusion. In some embodiments, the diagnostic conjugate is administered to the subject by injection. In some embodiments, the diagnostic conjugate is administered by bolus, slow bolus or slow infusion. In some embodiments, the therapeutic conjugate is administered by bolus, slow bolus or slow infusion. In some embodiments, the diagnostic conjugate is administered by bolus and the therapeutic conjugate is administered by slow bolus or slow infusion. In some embodiments, the therapeutic conjugate is infused over a period of minutes or hours, such as about 1 minute, about 2 minutes, about 5 minutes, about 10 minutes, about 15 minutes, about 20 minutes, about 25 minutes, about 30 minutes, about 35 minutes, about 40 minutes, about 45 minutes, about 55 minutes, about 1 hour, about 2 hours, about 3 hours, about 4 hours, about 5 hours, about 6 hours, about 7 hours, or about 8 hours. In particular embodiments, the therapeutic conjugate is infused over a period of about 30 minutes. In some embodiments, the diagnostic conjugate is infused over a period of minutes, such as about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, about 25 minutes, about 30 minutes, or less. In particular embodiments, the diagnostic conjugate is infused over a period of about 5 minutes or less.

In some embodiments, the treatment results in stable disease, partial remission or complete remission. In some embodiments, the treatment results in a reduction in metastases of the cancer in the subject. In some embodiments, the treatment results in a reduction in volume, size or growth of a tumor in the subject. In some embodiments, the treatment results in an increased responsiveness of the cancer to a subsequently administered anti-cancer agent.

In some embodiments, the amount of the therapeutic conjugate that is present in kidney tissue at 24 hours, 48 hours or 72 hours after administration of the conjugate is lower than the amount of the therapeutic conjugate that is present in kidney tissue at one hour after administration of the conjugate. In some embodiments, the ratio of the amount of the therapeutic conjugate in a primary tumor to the amount of the therapeutic conjugate in kidney tissue at 24 hours, 48 hours or 72 hours after administration of the conjugate is higher than the ratio of the amount of the therapeutic conjugate in the primary tumor to the amount of the therapeutic conjugate in kidney tissue at 1 hour after administration of the conjugate.

In another aspect, the present disclosure provides a pharmaceutical composition comprising a peptide having the amino acid sequence GNGVPNLRGDLQVLGQRVGRT.

In some embodiments, a PEG moiety is covalently attached at the N-terminus, the C-terminus or both the N- and C-termini of the peptide. In some embodiments, the PEG moiety is independently selected from the group consisting of PEG11, PEG12 (PEG 800), PEG28 (PEG 1500), and $(PEG28)_2$ (PEG 1500×2). In other embodiments, a first PEG moiety is covalently attached to the N-terminus of the peptide and a second PEG moiety is covalently attached to the C-terminus of the peptide, and the first PEG moiety and the second PEG moiety are independently selected from the group consisting of PEG11, PEG12 (PEG 800), PEG28 (PEG 1500), and $(PEG28)_2$ (PEG 1500×2). In some instances, the first PEG moiety and the second PEG moiety are the same. In particular instances, the first PEG moiety and the second PEG moiety each comprises PEG28 (PEG 1500). In some embodiments, the PEG moiety covalently attached to the C-terminus of the peptide terminates in an amide, a carboxyl group or a hydroxyl group.

In some embodiments, the peptide is covalently attached to an albumin binding moiety (ABM). In particular embodiments, the ABM comprises 4-(4-iodophenyl)butyric acid. In some embodiments, the ABM includes a linker, such as a peptide linker that is covalently attached to the peptide, the first PEG moiety, or the second PEG moiety. In certain embodiments, the ABM comprises a K(D-Abu-iodophenylbutyryl) moiety.

In some embodiments, the peptide is covalently attached to a chelating moiety. In particular embodiments, the chelating moiety is DOTA. In certain instances, a radionuclide is complexed with the chelating moiety. In some embodiments, a radionuclide is covalently attached directly or indirectly to the peptide. In some instances, the radionuclide is selected from the group consisting of $^{32}$P, $^{47}$Sc, $^{67}$Cu, $^{89}$Sr, $^{90}$Y, $^{105}$Rh, $^{111}$Ag, $^{117m}$Sn, $^{131}$I, $^{149}$Pm, $^{153}$Sm, $^{166}$Ho, $^{177}$Lu, $^{186}$Re, $^{188}$Re, $^{211}$At, and $^{212}$Bi. In other instances, the radionuclide is selected from the group consisting of $^{11}$C, $^{13}$N, $^{15}$O, $^{18}$F, $^{55}$Co, $^{60}$Cu, $^{61}$Cu, $^{62}$Cu, $^{64}$Cu, $^{66}$Ga, $^{67}$Cu, $^{68}$Ga, $^{82}$Rb, $^{86}$Y, $^{111}$In, $^{124}$I, $^{125}$I, or $^{131}$I. In other instances, the radionuclide is $^{177}$Lu or $^{68}$Ga.

In a related aspect, the present disclosure provides a pharmaceutical composition comprising a conjugate of Formula I (Formula I)

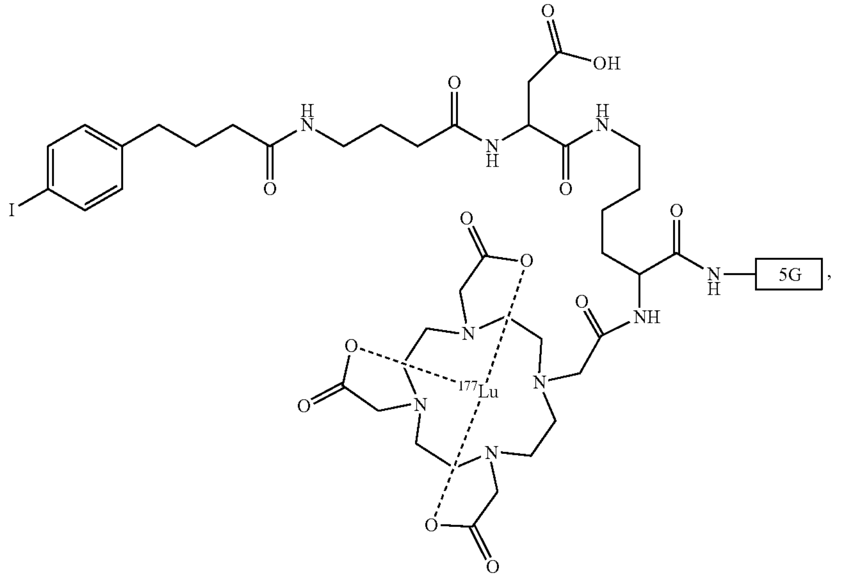

wherein 5G is a PEGylated peptide having the amino acid sequence GNGVPNLRGDLQVLGQRVGRT and comprising a first PEG moiety at the N-terminus of the peptide and a second PEG moiety at the C-terminus of the peptide; and a pharmaceutically acceptable excipient.

In some embodiments, the first PEG moiety and the second PEG moiety are independently selected from the group consisting of PEG11, PEG12 (PEG 800), PEG28 (PEG 1500), and $(PEG28)_2$ (PEG 1500×2). In some embodiments, the first PEG moiety and the second PEG moiety are the same. In particular embodiments, the first PEG moiety and the second PEG moiety each comprises PEG28 (PEG 1500).

In some embodiments, the composition contains between about 25 mCi and about 200 mCi radioactivity. In particular embodiments, the composition contains 25 mCi, 50 mCi, 100 mCi, 150 mCi, or 200 mCi radioactivity.

In another related aspect, the present disclosure provides a pharmaceutical composition comprising a conjugate of Formula II (Formula II)

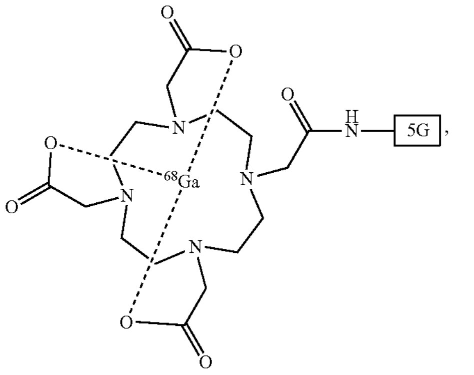

wherein 5G is a PEGylated peptide having the amino acid sequence GNGVPNLRGDLQVLGQRVGRT and comprising a first PEG moiety at the N-terminus of the peptide and a second PEG moiety at the C-terminus of the peptide; and a pharmaceutically acceptable excipient.

In some embodiments, the first PEG moiety and the second PEG moiety are independently selected from the group consisting of PEG11, PEG12 (PEG 800), PEG28 (PEG 1500), and $(PEG28)_2$ (PEG 1500×2). In some embodiments, the first PEG moiety and the second PEG moiety are the same. In particular embodiments, the first PEG moiety and the second PEG moiety each comprises PEG28 (PEG 1500).

In some embodiments, the composition contains up to about 5 mCi (e.g., greater than about 0.01 mCi to about 5 mCi) radioactivity.

BRIEF DESCRIPTION OF THE DRAWINGS

FIGS. 1A-1B show ELISA binding curves of peptide 1 (DOTA-5G) (FIG. 1A) and peptide 2 (DOTA-ABM-5G) (FIG. 1B) for integrin $\alpha_v\beta_6$ against biotinylated LAP (n=3/integrin/concentration; bars: SD). FIG. 1C shows cell-binding and internalization of $^{68}$ Ga-1 and $^{177}$Lu-2 at 37° C. using integrin $\alpha_v\beta_6$(+) BxPC-3 cells. The internalized fraction is a fraction of the total bound radioactivity (n=3/cell line; 1 h); bars: SD. FIG. 1D shows the percent radioactivity retained to determine efflux of $^{177}$Lu-2 from BxPC-3 cells at 37° C.

FIGS. 8A-8B show therapeutic efficacy of $^{177}$Lu-2 in mice bearing $\alpha_v\beta_6$ (+) BxPC-3 tumors, as determined by tumor volume measurement (FIG. 8A) and survival data (FIG. 8B). Group 1=Saline control (n=5), Group 2=Peptide 2 control (n=5), Group 3=74 MBq $^{177}$Lu-2 (n=10), and Group 4=2*37 MBq $^{177}$Lu-2 (n=7). Mice received first treatment 14 days post-tumor implant (Group 3) and 21 days post-tumor implant (Group 4) and were monitored up to 120 days post-treatment.

DETAILED DESCRIPTION

I. Introduction

Figure 2:
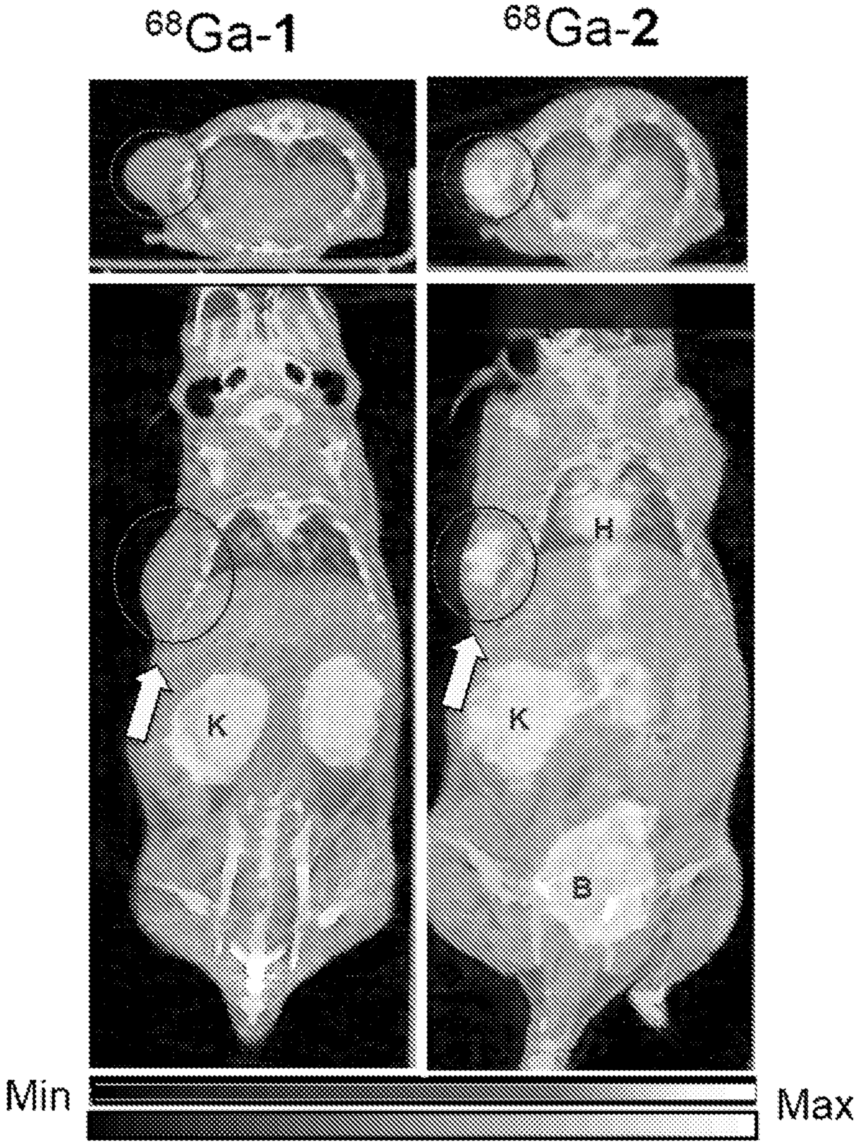
FIG. 2 shows representative transaxial (top) and coronal (bottom) PET/CT cross sections of mice bearing BxPC-3 tumors (arrow) obtained at 2 hours after injection of $^{68}$Ga-1 or $^{68}$Ga-2. K=Kidneys, B=Bladder, H=Heart. PET scale top bar and CT scale bottom bar below images.

Provided herein are methods and related compositions that incorporate a molecularly targeted approach via the integrin subtype $\alpha_v\beta_6$ using Peptide Receptor Radionuclide Therapy (PRRT) and a theranostic approach.

The integrin subtype $\alpha_v\beta_6$ is an epithelial-specific cell surface receptor that is undetectable in healthy adult epithelium but is significantly up-regulated in a wide range of epithelial-derived cancers, including pancreatic ductal adenocarcinoma (PDAC). $\alpha_v\beta_6$ was initially identified in PDAC and almost all tumors demonstrate highly upregulated expression of $\alpha_v\beta_6$.

PRRT is a therapy that employs a cell-targeting peptide combined with a radionuclide. When injected into the patient's bloodstream, the radioactive peptide delivers a targeted high dose of radiation directly to the cancer cells.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present disclosure. For purposes of the present disclosure, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a conjugate" includes a plurality of such conjugates, and so forth.

The term "about" is used herein to modify a numerical value and indicate a defined range around that value. If "X" is the value, "about X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. When "about" is applied to the first value of a set of values, it applies to all values in that set.

The term "peptide" refers to a compound made up of a single chain of D- or L-amino acids or a mixture of D- and L-amino acids joined by peptide bonds. Generally, peptides are about 2 to about 50 amino acids in length. As non-limiting examples, the peptides present in the conjugates described herein are between about 5 to about 45 amino acids in length, between about 8 to about 45 amino acids in length, between about 8 to about 25 amino acids in length, between about 8 to about 20 amino acids in length, between about 12 to about 45 amino acids in length, between about 12 to about 30 amino acids in length, or about 20 amino acids in length.

The term "RGD peptide" refers to the binding/interaction of a peptide motif in a conjugate described herein which shows the capacity of specific interaction with $\alpha_v\beta_6$ integrin. In some embodiments, the RGD peptide interacts with and/or binds to $\alpha_v\beta_6$ integrin without cross-reacting with molecules of similar sequences or structures. In some instances, the RGD peptide specifically binds to $\alpha_v\beta_6$ integrin when it binds with a substantially lower dissociation constant (i.e., tighter binding) than a molecule of similar sequence or structure. For example, in certain instances, a specific binding occurs when the RGD peptide binds to $\alpha_v\beta_6$ integrin with an about 2, 3, 4, 5, 6, 8, 10, 15, 20, 25, 30, 40, 50, 100, or 1000-fold or greater affinity than a related molecule. The binding of the RGD peptide to $\alpha_v\beta_6$ integrin may occur via intermolecular forces such as ionic bonds, hydrogen bonds, hydrophobic interactions, dipole-dipole bonds, and/or Van der Waals forces. Cross-reactivity may be tested, for example, by assessing binding of the RGD peptide under conventional conditions to $\alpha_v\beta_6$ integrin as well as to a number of more or less (e.g., structurally and/or functionally) closely related molecules. These methods may include, without limitation, binding studies, blocking and competition studies with closely related molecules, FACS analysis, surface plasmon resonance (e.g., with BIAcore), analytical ultracentrifugation, isothermal titration calorimetry, fluorescence anisotropy, fluorescence spectroscopy, radiolabeled ligand binding assays, and combinations thereof.

As used herein, the term "PEGylation" refers to the process of covalently coupling a polyethylene glycol (PEG) molecule to another molecule, e.g., an RGD peptide, which is then referred to as "PEGylated." As a non-limiting example, an RGD peptide may be PEGylated at both the amino-terminus and the carboxyl terminus with monodisperse PEG molecules having a defined chain length to generate bi-terminal PEGylated peptide conjugates. Monodisperse PEG molecules typically comprise discrete molecular weights with an exactly defined number of repeating ethylene glycol units. PEG moieties suitable for use are commercially available from Polypure AS (Oslo, Norway), which supplies monodisperse PEG molecules and PEG derivatives thereof consisting of substantially one oligomer only (e.g., greater than about 90%, 91%, 92%, 93%, 94%, 95%, 96%, 97%, 98%, or 99% oligomer purity). In particular embodiments, the RGD peptide is PEGylated at both ends with a single type or mixtures of different types of monodisperse PEG moieties having a molecular weight of less than about 5,000 daltons (Da) (e.g., less than about 5,000, 4,000, or 3,000 Da), such as, e.g., $PEG_{11}$, $PEG_{12}$ (PEG 800), $PEG_{28}$ (PEG 1500), and/or $(PEG_{28})_2$ (PEG 1500×2).

The term "radionuclide" is intended to include any nuclide that exhibits radioactivity. A "nuclide" refers to a type of atom specified by its atomic number, atomic mass, and energy state, such as carbon 14 ($^{14}$C). "Radioactivity" refers to the radiation, including alpha particles, beta particles, nucleons, electrons, positrons, neutrinos, and gamma rays, emitted by a radioactive substance. Examples of radionuclides suitable for use in the conjugates described herein include, but are not limited to, tritium ($^{3}$H), fluorine 18 ($^{18}$F), phosphorus 32 ($^{32}$P), sulfur 35 ($^{35}$S), scandium 47 ($^{47}$Sc), cobalt 55 ($^{55}$Co), copper 60 ($^{60}$Cu), copper 61 ($^{61}$Cu), copper 62 ($^{62}$Cu), copper 64 ($^{64}$Cu), gallium 66 ($^{66}$Ga), copper 67 ($^{67}$Cu), gallium 67 ($^{67}$Ga), gallium 68 ($^{68}$Ga), rubidium 82 ($^{82}$Rb), yttrium 86 ($^{86}$Y), yttrium 87 ($^{87}$Y), strontium 89 ($^{89}$Sr), strontium 90 ($^{99}$Sr), yttrium 90 ($^{90}$Y), rhodium 105 ($^{105}$Rh) silver 111 ($^{111}$Ag), indium 111 ($^{111}$In), iodine 124 ($^{124}$I), iodine 125 ($^{125}$I), iodine 131 ($^{131}$I), tin 117m ($^{117}$Sm), technetium 99m ($^{99m}$Tc), cesium 137 ($^{137}$Cs), promethium 149 ($^{149}$Pm), samarium 153 ($^{153}$Sm), holmium 166 ($^{166}$Ho), lutetium 177 ($^{177}$Lu), rhenium 186 ($^{186}$Re), rhenium 188 ($^{188}$Re), thallium 201 ($^{201}$Tl), astatine 211 ($^{211}$At), astatine 215 ($^{215}$At), astatine 217 ($^{217}$At), astatine 218 ($^{218}$At), bismuth 209 ($^{209}$Bi), bismuth 211 ($^{211}$Bi), bismuth 212 ($^{212}$Bi), bismuth 213 ($^{213}$Bi), polonium 210 ($^{210}$Po), polonium 211 ($^{211}$Po), polonium 212 ($^{212}$Po), polonium 214 ($^{214}$Po), polonium 215 ($^{215}$Po), polonium 216 ($^{216}$Po), polonium 218 ($^{218}$Po), radon 218 ($^{218}$Rn), radon 219 ($^{219}$Rn), radon 220 ($^{220}$Rn), radon 222 ($^{222}$Rn)) radon 226 ($^{226}$Rn), francium 221 ($^{221}$Fr), radium 223 ($^{223}$Ra), radium 224 ($^{224}$Ra), radium 226 ($^{226}$Ra), actinium 225 ($^{225}$Ac), actinium 227 ($^{227}$Ac), thorium 227 ($^{227}$Th), thorium 228 ($^{228}$Th), thorium 229 ($^{229}$Th), thorium 230 ($^{230}$Th), thorium 232 ($^{232}$Th), protactinium 231 ($^{231}$Pa), uranium 233 ($^{233}$U), uranium 234 ($^{234}$U), uranium 235 ($^{235}$U), uranium 236 ($^{236}$U), uranium 238 ($^{238}$U), neptunium 237 ($^{237}$Np), plutonium 238 ($^{238}$Pu), plutonium 239 ($^{239}$Pu), plutonium 240 ($^{240}$Pu), plutonium 244 ($^{244}$Pu), americium 241 ($^{241}$Am), curium 244 ($^{244}$Cm), curium 245 ($^{245}$Cm), curium 248 ($^{248}$Cm), californium 249 ($^{249}$Cf), and californium 252 ($^{252}$Cf). As used herein, the "m" in $^{117m}$Sn and $^{99m}$Tc stands for the meta state. Additionally, naturally-occurring radioactive elements such as uranium, radium, and thorium, which typically represent mixtures of radioisotopes, are suitable examples of radionuclides. $^{67}$Cu, $^{131}$I, $^{177}$Lu, and $^{186}$Re are beta- and gamma-emitting radionuclides. $^{212}$Bi is an alpha- and beta-emitting radionuclide. $^{226}$Ra is an alpha- and gamma-emitting radionuclide. $^{211}$At, $^{215}$At, $^{217}$At, $^{218}$At, $^{209}$Bi, $^{211}$Bi, $^{213}$Bi, $^{210}$Po, $^{211}$Po, $^{212}$Po, $^{214}$Po, $^{215}$Po, $^{216}$Po, $^{218}$Po, $^{218}$Po, $^{219}$Rn, $^{220}$Rn, $^{222}$Rn, $^{226}$Rn, $^{221}$Fr, $^{223}$Ra, $^{224}$Ra, $^{225}$Ac, $^{227}$Ac, $^{227}$Th, $^{228}$Th, $^{229}$Th, $^{230}$Th, $^{232}$Th, $^{231}$Pa, $^{233}$U, $^{234}$U, $^{235}$U, $^{236}$U, $^{238}$U, $^{237}$Np, $^{238}$Pu, $^{239}$Pu, $^{240}$Pu, $^{244}$Pu, $^{241}$Am, $^{244}$Cm, $^{245}$Cm, $^{248}$Cm, $^{249}$Cf, and $^{252}$Cf are examples of alpha-emitting radionuclides. $^{3}$H, $^{32}$P, $^{35}$S, $^{47}$Sc, $^{89}$Sr, $^{90}$Sr, $^{90}$Y, $^{105}$Rh, $^{111}$Ag, $^{117m}$Sn, $^{149}$Pm, $^{153}$Sm, $^{166}$Ho, and $^{188}$Re are examples of beta-emitting radionuclides. $^{67}$Ga, $^{111}$In, $^{99m}$Tc, $^{137}$Cs, and $^{201}$Tl are examples of gamma-emitting radionuclides. $^{55}$Co, $^{60}$Cu, $^{61}$Cu, $^{62}$Cu, $^{66}$Ga, $^{68}$Ga, $^{82}$Rb, and $^{86}$Y are examples of positron-emitting radionuclides. $^{64}$Cu is a beta- and positron-emitting radionuclide.

The term "subject" or "patient" typically refers to humans, but can also include other animals such as, e.g., other primates, rodents, canines, felines, equines, ovines, porcines, and the like.

As used herein, the term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a conjugate described herein is administered at the same time, just prior to, or just after the administration of a second agent.

III. RGD Peptides and Conjugates

Provided herein are PRRT methods using a therapeutic conjugate for PRRT where the conjugate binds an $\alpha_v\beta_6$ integrin. The conjugates for use with the methods herein comprise an RGD peptide that is selective for binding $\alpha_v\beta_6$ integrin. In some embodiments, the peptide comprises the RGD motif, $RGDLX_1X_2X_3$, wherein $X_1$ and $X_2$ are independently selected amino acids, and $X_3$ is L or I. In certain embodiments, the RGD peptide does not comprise any alanine residues. In certain embodiments, the RGD peptide is between 8 and 40 amino acids. In some cases, the RGD peptide is more than 20 amino acids. In some cases, the RGD peptide is 21 amino acids. In certain embodiments, the RGD peptide further comprises $QX_4VX_5RT$ that is positioned C-terminally to the RGD motif, wherein $X_4$ is R or K and $X_5$ is A or G. In some cases, the RGD peptide comprises the amino acid sequence QRVGRT positioned C-terminal to the RGD motif. In some cases, the RGD peptide comprises the amino acid sequence RGDLQVLGQRVGRT. In certain embodiments, the RGD peptide comprises the amino acid sequence GNGVPNLRGDLQVLGQRVGRT. In certain embodiments, the RGD peptide consists or consists essentially of the amino acid sequence GNGVPNLRGDLQVLGQRVGRT.

In some embodiments, the conjugate also comprises one or more polyethylene glycol (PEG) moieties covalently attached to the RGD peptide. In some cases, the conjugate comprises two PEG moieties, e.g., one PEG moiety is covalently attached to the N-terminus of the peptide and one PEG moiety is covalently attached to the C-terminus of the peptide. In certain embodiments, the conjugate comprises the amino acid sequence GNGVPNLRGDLQVLGQRVGRT with a first PEG moiety covalently attached to the N-terminus of the peptide and a second PEG moiety covalently attached to the C-terminus of the peptide. In some embodiments, the PEG moiety covalently attached to the C-terminus of the peptide terminates in an amide, a carboxyl group or a hydroxyl group.

In some embodiments, the first PEG moiety and the second PEG moiety each have a molecular weight of less than about 5000 daltons (Da), e.g., less than about 3000 Da. In certain embodiments, the first PEG moiety and the second PEG moiety are monodisperse PEG moieties having a defined chain length. Non-limiting examples of PEG moieties having a defined chain length include small, monodisperse PEG molecules having greater than about 95% oligomer purity. In certain instances, the first PEG moiety and the second PEG moiety are independently selected from the group consisting of $PEG_{11}$, $PEG_{12}$ (PEG 800), $PEG_{28}$ (PEG 1500), and $(PEG_{28})_2$ (PEG 1500×2). In particular embodiments, the first PEG moiety and the second PEG moiety are the same. In certain embodiments, the first PEG moiety and the second PEG moiety are both $PEG_{28}$ (PEG 1500). In certain embodiments, the conjugate comprises the amino acid sequence GNGVPNLRGDLQVLGQRVGRT with the N- and C-terminus of the peptide each having a $PEG_{28}$ (PEG 1500) moiety covalently attached thereto (also referred to herein as "5G"). In some embodiments, the $PEG_{28}$ (PEG 1500) moiety covalently attached to the C-terminus of the peptide terminates in an amide, a carboxyl group or a hydroxyl group.

In some embodiments, the conjugate includes an albumin binding moiety (ABM) covalently attached to the conjugate. The ABM may increase the half-life of the conjugate in serum, such as when administered to a subject. In some embodiments, the ABM is covalently attached to the peptide, the first PEG moiety, or the second PEG moiety. In some embodiments, the ABM includes a linker, such as a peptide linker that is covalently attached to the peptide, the first PEG moiety, or the second PEG moiety. In certain embodiments, the ABM comprises 4-(4-iodophenyl)butyric acid (IPA) or a homolog thereof with a shorter alkyl chain such as, e.g., 4-(4-iodophenyl)propionic acid or 4-(4-iodophenyl)acetic acid, or the ABM comprises 4-(4-methylphenyl)butyric acid or 4-(4-bromophenyl)butyric acid or a homolog thereof with a shorter alkyl chain such as, e.g., a propionic acid or acetic acid homolog thereof. In certain instances, the ABM is covalently attached to the first and/or second PEG moiety via a linker such as a glutamic acid (E) linker, a peptide linker such as a lysine-aspartic acid-aminobutyric acid (K-D-Abu) linker, or other suitable linker (e.g., amino acid or peptide linker) known to one of skill in the art. In certain embodiments, the ABM comprises an ε-(4-(4-iodophenyl)butyl amide)lysine-glutamic acid moiety ("K(IPA)E"), which corresponds to IPA that is covalently attached to the side-chain of the lysine residue of a lysine-glutamic acid peptide linker. In certain other embodiments, the ABM comprises a K(D-Abu-iodophenylbutyryl) moiety, which corresponds to IPA that is covalently attached to the aminobutyric acid of a lysine-aspartic acid-aminobutyric acid (K-D-Abu) peptide linker. In some embodiments, the ABM comprising the K(IPA)E or K(D-Abu-iodophenylbutyryl) moiety is covalently attached to the first PEG moiety. In certain embodiments, the conjugate comprises the amino acid sequence GNGVPNLRGDLQVLGQRVGRT with the N- and C-terminus of the peptide each having a PEG moiety, such as a $PEG_{28}$ (PEG 1500) moiety, covalently attached thereto, and the conjugate further comprises an ABM covalently attached thereto. In some embodiments, the PEG moiety covalently attached to the C-terminus of the peptide terminates in an amide, a carboxyl group or a hydroxyl group.

In other embodiments, an imaging agent or therapeutic agent is covalently attached (e.g., via a prosthetic group, a chelating agent, or a linker) to an albumin binding motif that is covalently attached to the first PEG moiety, such that the imaging agent or therapeutic agent is the most N-terminal moiety in the conjugate. In certain embodiments, the conjugate comprises a peptide having the amino acid sequence GNGVPNLRGDLQVLGQRVGRT with the N- and C-terminus of the peptide each having a PEG moiety, such as a $PEG_{28}$ (PEG 1500) moiety, covalently attached thereto, an ABM covalently attached to the PEG moiety at the N-terminus of the peptide and a therapeutic agent covalently attached at the N-terminus of the conjugate. In certain embodiments, the conjugate comprises a peptide having the amino acid sequence GNGVPNLRGDLQVLGQRVGRT with the N- and C-terminus of the peptide each having a PEG moiety, such as a $PEG_{28}$ (PEG 1500) moiety, covalently attached thereto, an ABM covalently attached to the PEG moiety at the N-terminus of the peptide and an imaging agent covalently attached at the N-terminus of the conjugate. In some embodiments, the PEG moiety covalently attached to the C-terminus of the peptide terminates in an amide, a carboxyl group or a hydroxyl group.

In some embodiments, the conjugate is a therapeutic conjugate and comprises a therapeutic agent. In some embodiments, the therapeutic agent is a radionuclide such as an alpha-, beta-, and/or gamma-emitting radionuclide. In some embodiments, the therapeutic conjugate herein comprises a radionuclide such as $^{3}H$, $^{18}F$, $^{32}P$, $^{35}S$, $^{47}Sc$, $^{55}Co$, $^{60}Cu$, $^{61}Cu$, $^{62}Cu$, $^{64}Cu$, $^{66}Ga$, $^{67}Cu$, $^{67}Ga$, $^{68}Ga$, $^{82}Rb$, $^{86}Y$, $^{87}Y$, $^{89}Sr$, $^{90}Sr$, $^{90}Y$, $^{105}Rh$, $^{111}Ag$, $^{111}In$, $^{124}I$, $^{125}I$, $^{131}I$, $^{117m}Sn$, $^{99m}Tc$, $^{137}Cs$, $^{149}Pm$, $^{153}Sm$, $^{166}Ho$, $^{177}Lu$, $^{186}Re$, $^{188}Re$, $^{201}Tl$, $^{211}At$, $^{215}At$, $^{217}At$, $^{218}At$, $^{209}Bi$, $^{211}Bi$, $^{212}Bi$, $^{213}Bi$, $^{210}Po$, $^{211}Po$, $^{212}Po$, $^{214}Po$, $^{215}Po$, $^{216}Po$, $^{218}Po$, $^{218}Rn$, $^{219}Rn$, $^{220}Rn$, $^{222}Rn$, $^{226}Rn$, $^{221}Fr$, $^{223}Ra$, $^{224}Ra$, $^{226}Ra$, $^{225}Ac$, $^{227}Ac$, $^{227}Th$, $^{228}Th$, $^{229}Th$, $^{230}Th$, $^{232}Th$, $^{231}Pa$, $^{233}U$, $^{234}U$, $^{235}U$, $^{236}U$, $^{238}U$, $^{237}Np$, $^{238}Pu$, $^{239}Pu$, $^{240}Pu$, $^{244}Pu$, $^{241}Am$, $^{244}Cm$, $^{245}Cm$, $^{248}Cm$, $^{249}Cf$, and $^{252}Cf$.

In some embodiments, the therapeutic conjugate herein comprises a radionuclide such as $^{32}P$, $^{47}Sc$, $^{67}Cu$, $^{89}Sr$, $^{90}Y$, $^{105}Rh$, $^{111}Ag$, $^{117m}Sn$, $^{131}I$, $^{149}Pm$, $^{153}Sm$, $^{166}Ho$, $^{177}Lu$, $^{186}Re$, $^{188}Re$, $^{211}At$, and $^{212}Bi$. In particular embodiments, the radionuclide is $^{177}Lu$. In some embodiments, the conjugate has the structure of Formula I, wherein 5G is a bi-PEGylated RGD peptide.

(Formula I)

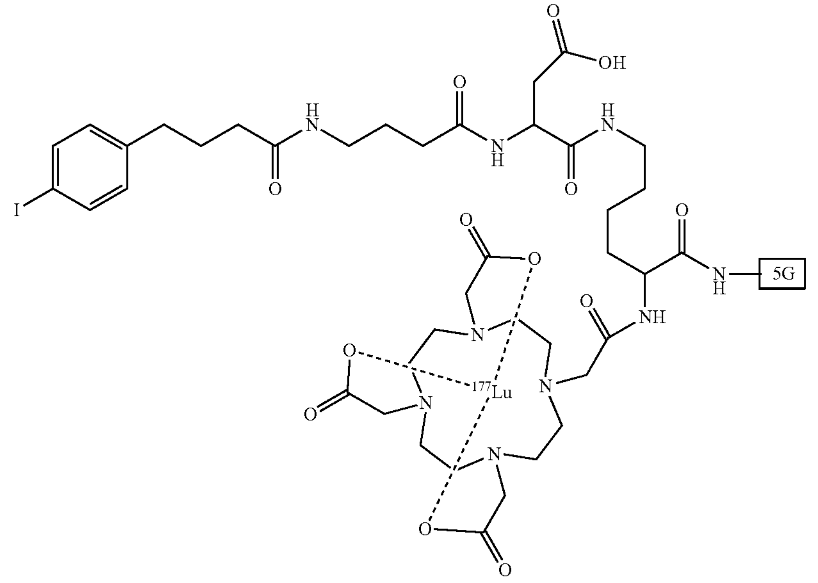

In some embodiments, the conjugate has the structure of Formula I, wherein 5G is a bi-pegylated RGD peptide and the RGD peptide has the amino acid sequence GNGVPNLRGDLQVLGQRVGRT, such as $PEG_{28}$-GNGVPNLRGDLQVLGQRVGRT-$PEG_{28}$-C(O)$NH_2$.

In certain embodiments, the conjugate comprises a peptide having the amino acid sequence GNGVPNLRGDLQVLGQRVGRT with the N- and C-terminus of the peptide each having a PEG moiety, such as a $PEG_{28}$ (PEG 1500) moiety, covalently attached thereto, an ABM covalently attached to the PEG moiety at the N-terminus of the peptide and a chelating moiety for complexing a radionuclide. In some embodiments, the PEG moiety covalently attached to the C-terminus of the peptide terminates in an amide, a carboxyl group or a hydroxyl group. In some aspects, the chelating moiety is a DOTA moiety (1,4,7,10-tetraazacyclododecane-1,4,7,10-tetraacetic acid) covalently attached to the conjugate. In some aspects, the chelating moiety of the conjugate is not complexed with a radionuclide. In some aspects, the chelating moiety of the conjugate is complexed with a radionuclide. In some aspects, the chelating moiety of the conjugate is complexed with a radionuclide, and the radionuclide is selected for use as a therapeutic agent, such as $^{32}P$, $^{47}Sc$, $^{67}Cu$, $^{89}Sr$, $^{90}Y$, $^{105}Rh$, $^{111}Ag$, $^{117m}Sn$, $^{131}I$, $^{149}Pm$, $^{153}Sm$, $^{166}Ho$, $^{177}Lu$, $^{186}Re$, $^{188}Re$, $^{211}At$, and $^{212}Bi$. In some aspects, the chelating moiety of the conjugate is complexed with a radionuclide, and the radionuclide is $^{177}Lu$. In some aspects, the chelating moiety of the conjugate is complexed with a radionuclide, and the radionuclide is selected for use as an imaging agent, such as $^{11}C$, $^{13}N$, $^{15}O$, $^{18}F$, $^{55}Co$, $^{60}Cu$, $^{61}Cu$, $^{62}Cu$, $^{64}Cu$, $^{66}Ga$, $^{67}Cu$, $^{68}Ga$, $^{82}Rb$, $^{86}Y$, $^{111}In$, $^{124}I$, $^{125}I$, or $^{131}I$. In particular embodiments, the radionuclide is $^{68}Ga$.

In certain embodiments, the conjugate comprises a peptide having the amino acid sequence GNGVPNLRGDLQVLGQRVGRT with the N- and C-terminus of the peptide each having a PEG moiety, such as a $PEG_{28}$ (PEG 1500) moiety, covalently attached thereto, and a chelating moiety for complexing a radionuclide. In some embodiments, the PEG moiety covalently attached to the C-terminus of the peptide terminates in an amide, a carboxyl group or a hydroxyl group. In some aspects, the chelating moiety is a DOTA moiety (1,4,7,10-tetraazacyclododecane-1,4,7,10-tetraacetic acid) covalently attached to the conjugate. In some aspects, the chelating moiety of the conjugate is not complexed with a radionuclide. In some aspects, the chelating moiety of the conjugate is complexed with a radionuclide. In some aspects, the chelating moiety of the conjugate is complexed with a radionuclide, and the radionuclide is selected for use as a therapeutic agent, such as $^{32}P$, $^{47}Sc$, $^{67}Cu$, $^{89}Sr$, $^{90}Y$, $^{105}Rh$, $^{111}Ag$, $^{117m}Sn$, $^{131}I$, $^{149}Pm$, $^{153}Sm$, $^{166}Ho$, $^{177}Lu$, $^{186}Re$, $^{188}Re$, $^{211}At$, and $^{212}Bi$. In some aspects, the chelating moiety of the conjugate is complexed with a radionuclide, and the radionuclide is $^{177}Lu$. In some aspects, the chelating moiety of the conjugate is complexed with a radionuclide, and the radionuclide is selected for use as an imaging agent, such as $^{11}C$, $^{13}N$, $^{15}O$, $^{18}F$, $^{55}Co$, $^{60}Cu$, $^{61}Cu$, $^{62}Cu$, $^{64}Cu$, $^{66}Ga$, $^{67}Cu$, $^{68}Ga$, $^{82}Rb$, $^{86}Y$, $^{111}In$, $^{124}I$, $^{125}I$, or $^{131}I$. In particular embodiments, the radionuclide is $^{68}Ga$.

In some embodiments, the therapeutic conjugate such as the conjugate of Formula I is provided in a pharmaceutical composition for administration. In some cases, the pharmaceutical composition comprises one or more unit doses, wherein the amount of radioactivity present in a dose is between about 25 mCi and about 200 mCi. In certain embodiments, the amount of radioactivity present in a dose of the conjugate is between about 25 mCi and about 50 mCi, about 25 mCi and about 100 mCi, about 25 mCi and about 150 mCi, about 25 mCi and about 200 mCi, about 50 mCi and about 100 mCi, about 50 mCi and about 150 mCi, about 50 mCi and about 200 mCi, about 100 mCi and about 150 mCi, about 100 mCi and about 200 mCi, or about 150 mCi and about 200 mCi. In some cases, the amount of radioactivity present in a unit dose is about 25 mCi, about 50 mCi, about 100 mCi, about 150 mCi or about 200 mCi. In some embodiments, the amount of peptide in each unit dose of the conjugate is no more than about 500 μg, about 400 μg, about 300 μg, about 200 μg, or about 100 μg of peptide. In some cases, the amount of peptide in each unit dose of the conjugate is no more than about 100 μg of peptide.

In some embodiments, the conjugate is a diagnostic conjugate and comprises a diagnostic agent. In some embodiments, the diagnostic agent is a radionuclide such as a positron-emitting radionuclide. In some embodiments, the diagnostic conjugate herein comprises a radionuclide such as $^{11}C$, $^{13}N$, $^{15}O$, $^{18}F$, $^{55}Co$, $^{60}Cu$, $^{61}Cu$, 62Cu, $^{64}Cu$, $^{66}Ga$, $^{67}Cu$, $^{68}Ga$, $^{82}Rb$, $^{86}Y$, $^{111}In$, $^{124}I$, $^{125}I$, or $^{131}I$. In particular embodiments, the radionuclide is $^{68}Ga$. In some embodiments, the conjugate has the structure of Formula II, wherein 5G is a bi-PEGylated RGD peptide comprising the amino acid sequence GNGVPNLRGDLQVLGQRVGRT.

(Formula II)

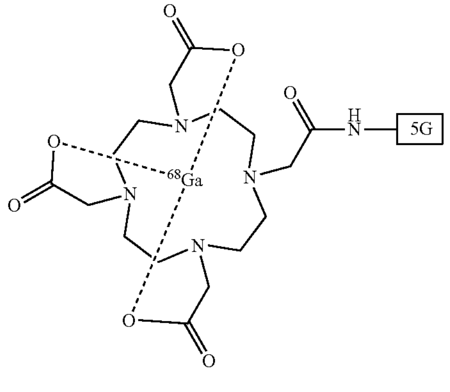

IV. Methods of Use

The methods herein include providing a therapeutically effective dose of a therapeutic conjugate as described herein to a subject. The therapeutic conjugates herein may comprise a radionuclide such as $^{177}Lu$. In some embodiments, the conjugate has the structure of Formula I, wherein 5G is a bi-PEGylated RGD peptide. In some embodiments, the RGD peptide (i.e., found within the conjugate having the structure of Formula I) has the amino acid sequence GNGVPNLRGDLQVLGQRVGRT, such as $PEG_{28}$-GNGVPNLRGDLQVLGQRVGRT-$PEG_{28}$-C(O)$NH_2$.

(Formula I)

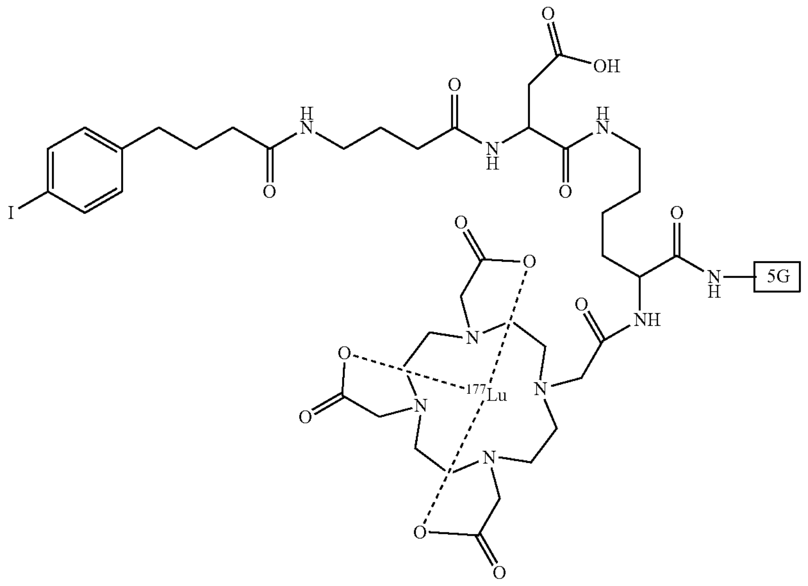

In some embodiments, the dose of the therapeutic conjugate administered to a subject contains between about 25 mCi and about 200 mCi radioactivity. In some embodiments, the dose of the conjugate contains between about 25 mCi and about 100 mCi radioactivity. In some embodiments, the dose of the therapeutic conjugate contains between about 25 mCi and about 150 mCi radioactivity. In some cases, the dose administered contains about 25 mCi, about 50 mCi, about 100 mCi, about 150 mCi, or about 200 mCi radioactivity. In some embodiments, the amount of peptide in the dose of the therapeutic conjugate is no more than about 500 μg, about 400 μg, about 300 μg, about 200 μg, or about 100 μg of peptide. In some cases, the amount of peptide administered in the dose of the therapeutic conjugate is no more than about 100 μg of peptide. In some embodiments, the dose of the therapeutic conjugate does not cause an adverse event (AE) in the subject, such as, e.g., an AE greater than or equal to grade 3 (i.e., severe AE). In some embodiments, the dose of the therapeutic conjugate does not exceed a radiation dose of about 23 Gy to the kidneys and/or a radiation dose of about 1.5 Gy to the bone marrow.

The therapeutic conjugate may be administered by infusion, such as over a period of time, such as minutes or hours. In some embodiments, the therapeutic conjugate is infused over a period of minutes, such as about 1 minute, about 2 minutes, about 5 minutes, about 10 minutes, about 15 minutes, about 20 minutes, about 25 minutes, about 30 minutes, about 35 minutes, about 40 minutes, about 45 minutes, or about 55 minutes. In some embodiments, the therapeutic conjugate is infused over a period of about 30 minutes. In some embodiments, the therapeutic conjugate is infused over a period of hours, such as about 1 hour, about 2 hours, about 3 hours, about 4 hours, about 5 hours, about 6 hours, about 7 hours, or about 8 hours. In some embodiments, the therapeutic conjugate is infused over a period of about 4 hours. In some embodiments, the therapeutic conjugate is co-infused with a solution of amino acids. In some cases, the infusion of the amino acid solution is commenced prior to the infusion of the therapeutic conjugate.

In some embodiments, the therapeutic conjugate is administered to a subject once, twice, three times, four times, or five times over a course of treatment. Subsequent administration of the therapeutic conjugate may occur at defined intervals of time, separated by days, weeks or months. In some cases, the therapeutic conjugate is administered at a subsequent time if the tumor or cancerous cells reappear, continue to grow or otherwise are not fully treated after the first administration of the therapeutic conjugate. In some cases, the therapeutic conjugate is administered again at a subsequent time if the subject does not have a complete response to the first treatment, experiences a partial response, a stable response or progressive disease.

In some embodiments, the dosimetry and/or biodistribution of the therapeutic conjugate is evaluated following administration of the therapeutic conjugate to a subject. As a non-limiting example, the dosimetry and biodistribution of the therapeutic conjugate can be evaluated using nuclear imaging at 1 day and/or 7 days after administration (e.g., infusion) to a subject. In some cases, the subject undergoes whole body planar imaging (e.g., anterior and posterior view) and single photon emission computerized tomography/computed tomography (SPECT/CT) (e.g., skull vertex extending through the perineum, terminating at the proximal thighs; approx. 2-4 bed positions) at about 24 and/or 168 hours following administration of the therapeutic conjugate. In some cases, serial blood samples are drawn at about 5, 15, 30, 60, 120 and/or 180 minutes following administration of the therapeutic conjugate e.g., for evaluation of biodistribution. In some cases, full chemistry, hematology, liver function tests, and/or EKG are performed at 1 day and/or 7 days (e.g., ±48 hours) following administration of the therapeutic conjugate.

Methods for dosimetry analysis are known in the art and include, but are not limited to, descriptive statistics (e.g., mean, median, standard deviation, etc.) reported for AUC based on activity concentration-time curves of the therapeutic conjugate (e.g., separately for discernible thoracic and abdominal organs, target lesion, and blood), maximum uptake (e.g., achieved in %) at the target lesion and in discernible organs, specific absorbed dose per organ (μGy/MBq), and cumulative absorbed organ doses (Gy). In some cases, organs receiving the highest absorbed dose assessed by equivalent dose to tissue are tabulated using frequency and proportion. In some cases, graphic tools are used to describe the endpoints.

In some embodiments, the distribution of the therapeutic conjugate is determined using whole-body planar SPECT/CT imaging. As a non-limiting example, radiation-absorbed doses to kidneys, stomach, uninvolved liver, bone marrow and the whole body together with any other organs displaying accumulation of the therapeutic conjugate are calculated based on the analysis of serial blood counts and SPECT/CT scans. In some cases, the SPECT/CT images are used to compute the volumetric absorbed radiation dose in the diseased and healthy tissues, e.g., activity concentration-time curves for normal tissues can be generated from region-of-interest (ROI) analysis from the SPECT/CT scans, activity concentration-time curves for red marrow and heart can be generated from blood activity concentration measured by a well scintillation counter, and/or volumes of interest (VOI) can be generated for each patient. In some cases, the activity concentration in red bone marrow is equal to that in blood. In some cases, activity concentration-time curves are integrated (e.g., either analytically or numerically as appropriate) to yield AUC values from which so-called residence times are generated. In some cases, these data are inputted into an organ dosimetry software (e.g., OLINDA/EXM) to generate absorbed dose estimates for normal tissues. In some cases, a supplementary dosimetry assessment is performed including, e.g., lesion absorbed dose estimates based on image ROI analysis. In some cases, absorbed doses are normalized to administered activity and expressed in terms of mGy/MBq.

In some embodiments, the distribution of the therapeutic conjugate in a tumor (e.g., a primary tumor or cancerous lesion), blood, gall bladder, liver, heart, lung, spleen, kidneys, pancreas, stomach, small intestines, bladder, skin, muscle, bone, large intestines, and/or brain of a subject is determined using, e.g., SPECT/CT imaging. In certain embodiments, the amount of the therapeutic conjugate that is present in a non-tumor tissue at 24 hours, 48 hours and/or 72 hours after administration of the conjugate is lower than the amount of the therapeutic conjugate that is present in the non-tumor tissue at one hour after administration of the conjugate. In certain embodiments, the ratio of the amount of the therapeutic conjugate in a tumor to the amount of the therapeutic conjugate in a non-tumor tissue at 24 hours, 48 hours and/or 72 hours after administration of the conjugate is higher than the ratio of the amount of the therapeutic conjugate in the tumor to the amount of the therapeutic conjugate in the non-tumor tissue at 1 hour after administration of the conjugate.

In some embodiments, the amount of the therapeutic conjugate that is present in kidney tissue at 24 hours, 48 hours and/or 72 hours after administration of the conjugate is lower than the amount of the therapeutic conjugate that is present in kidney tissue at one hour after administration of the conjugate. In some embodiments, the ratio of the amount of the therapeutic conjugate in a primary tumor to the amount of the therapeutic conjugate in kidney tissue at 24 hours, 48 hours and/or 72 hours after administration of the conjugate is higher than the ratio of the amount of the therapeutic conjugate in the primary tumor to the amount of the therapeutic conjugate in kidney tissue at 1 hour after administration of the conjugate.

In some embodiments, the amount of the therapeutic conjugate that is present in stomach tissue at 24 hours, 48 hours and/or 72 hours after administration of the conjugate is lower than the amount of the therapeutic conjugate that is present in stomach tissue at one hour after administration of the conjugate. In some embodiments, the ratio of the amount of the therapeutic conjugate in a primary tumor to the amount of the therapeutic conjugate in stomach tissue at 24 hours, 48 hours and/or 72 hours after administration of the conjugate is higher than the ratio of the amount of the therapeutic conjugate in the primary tumor to the amount of the therapeutic conjugate in stomach tissue at 1 hour after administration of the conjugate.

In some embodiments, the amount of the therapeutic conjugate that is present in large intestine tissue at 24 hours, 48 hours and/or 72 hours after administration of the conjugate is lower than the amount of the therapeutic conjugate that is present in large intestine tissue at one hour after administration of the conjugate. In some embodiments, the ratio of the amount of the therapeutic conjugate in a primary tumor to the amount of the therapeutic conjugate in large intestine tissue at 24 hours, 48 hours and/or 72 hours after administration of the conjugate is higher than the ratio of the amount of the therapeutic conjugate in the primary tumor to the amount of the therapeutic conjugate in large intestine tissue at 1 hour after administration of the conjugate.

In some embodiments, the amount of the therapeutic conjugate in liver tissue is minimal when assayed at 1 hour, 24 hours, 48 hours and/or 72 hours after administration of the conjugate. In some embodiments, the amount of the therapeutic conjugate in a primary tumor is substantially greater when compared to the amount of the therapeutic conjugate in liver tissue at 1 hour, 24 hours, 48 hours and/or 72 hours after administration of the conjugate.

In some embodiments of the methods herein, prior to administration of the therapeutic conjugate, a diagnostic conjugate is administered to the subject. The diagnostic conjugate comprises an RGD peptide that binds an $\alpha_v\beta_6$ integrin covalently attached (directly or indirectly) to a radionuclide. In some cases, the RGD peptide of the diagnostic conjugate has the same amino acid sequence as the RGD peptide present in the therapeutic conjugate. In some embodiments, the radionuclide of the diagnostic conjugate may have a shorter half-life as compared to the radionuclide of the therapeutic conjugate. In some cases, the radionuclide is $^{68}$Ga. In some cases, the radionuclide is $^{68}$Ga for the diagnostic conjugate and the therapeutic conjugate comprises the radionuclide $^{177}$Lu. In some embodiments, the diagnostic conjugate has the structure of Formula II.

(Formula II)

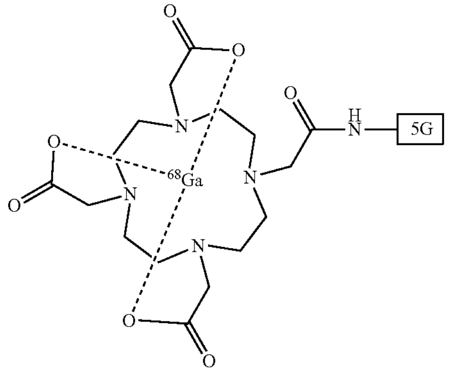

In some embodiments, the diagnostic conjugate has the structure of Formula II, wherein 5G is a bi-PEGylated RGD peptide. In some embodiments, the RGD peptide (i.e., found within the diagnostic conjugate having the structure of Formula II) has the amino acid sequence GNGVPNLRGDLQVLGQRVGRT, such as $PEG_{28}$-GNGVPNLRGDLQVLGQRVGRT-$PEG_{28}$-C(O)$NH_2$.

In some embodiments, the methods include administering a diagnostic conjugate of Formula II for diagnostic imaging of a tumor, cancerous lesion or cancerous cells. In some embodiments, the methods include administering a diagnostic conjugate of Formula II for diagnostic imaging of a tumor, cancerous lesion or cancerous cells and subsequently administering a therapeutic conjugate of Formula I to treat the tumor, cancerous lesion or cancerous cells. In some embodiments, the methods include administering a therapeutic conjugate of Formula I to treat a cancerous lesion when sufficient lesion uptake (e.g., any visualized lesion with a maximum standardized uptake value (SUVmax)>2-fold above normal lung or liver) of the diagnostic conjugate of Formula II is detected.

In some embodiments, the diagnostic conjugate is administered by injection. In some embodiments, the diagnostic conjugate is administered by infusion. In some embodiments, the diagnostic conjugate is infused over a period of minutes, such as about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, about 25 minutes, about 30 minutes, or less. In some embodiments, the diagnostic conjugate is infused over a period of about 5 minutes or less.

In some embodiments, the diagnostic conjugate may be imaged in the body or a portion of the body of the subject. In some embodiments, the uptake and accumulation of the diagnostic conjugate in a lesion, tissue or organ may be used to select subjects for administration of the therapeutic conjugate. In some embodiments, the diagnostic conjugate is utilized to select patients that have an $\alpha_v\beta_6$ integrin-related lesion or cancer cells and who are eligible for treatment with the therapeutic conjugate. In some embodiments, the diagnostic conjugate is utilized to select patients that have an $\alpha_v\beta_6$ integrin-related lesion or cancer cells and the selected patients then receive a dose of a therapeutic conjugate, such as the therapeutic conjugate of Formula I within 1 week, 2 weeks, 3 weeks, 4 weeks, 5 weeks or 6 weeks after imaging the diagnostic conjugate. In some embodiments, the diagnostic conjugate is utilized to select patients that have an $\alpha_v\beta_6$ integrin-related lesion or cancer cells and the selected patients then receive a dose of a therapeutic conjugate, such as the therapeutic conjugate of Formula I within 4 to 5 weeks after imaging the diagnostic conjugate.

In some embodiments, the general distribution of the diagnostic conjugate is determined by blood data and visual analysis of PET/CT scans. As a non-limiting example, reconstructed PET/CT images (e.g., skull apex to proximal-thigh whole body static) can be displayed on an imaging workstation, reoriented into maximum intensity projection (MIP), transaxial, coronal and sagittal images. In certain embodiments, PET, fused PET/CT and/or CT images are reviewed. In some embodiments, regions of interest (ROIs) are placed around tracer avid foci suspicious for malignancy and key organs (e.g., kidney, bladder, intestines, liver, spleen, lung, pancreas) in order to obtain SUV parameters, including SUVmax and SUV mean. In certain instances, SUV measurements are summarized using mean, median, range, and counts, and a repeated measures ANOVA model is used to relate the SUVs to the tissue regions. In some embodiments, "non-excreted" radioactivity and "excreted" radioactivity are tracked, wherein non-excreted radioactivity in the body is calculated from volume-of-interest (VOI) analysis to derive the amount of radioactivity in major organs, tissues of interest and the remainder of the body. In some cases, data are scaled to the "Reference Man" anthropomorphic model for dosimetry purposes. In some cases, organ activity is integrated over time to obtain the time-integrated activity coefficient. In some cases, an organ dosimetry software (e.g., OLINDA/EXM) is used to obtain dose and effective dose measurement.

Any device or method known in the art for detecting the radioactive emissions of radionuclides in a subject is suitable for use with the conjugates and methods described herein. For example, methods such as single photon emission computerized tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled conjugate described herein. Positron emission tomography (PET) is another suitable technique for detecting radiation in a subject. Furthermore, U.S. Pat. No. 5,429,133 describes a laparoscopic probe for detecting radiation concentrated in solid tissue tumors. Miniature and flexible radiation detectors intended for medical use are produced by Intra-Medical LLC (Santa Monica, CA). Furthermore, nuclear magnetic resonance (NMR)-based methods (e.g., magnetic resonance spectroscopy (MRS) and magnetic resonance imaging (MRI)) or any other imaging technique known to one of skill in the art (including, but not limited to, computed tomography (CT)) may be combined with methods that are suitable for detecting the radioactive emissions of radionuclides. In some embodiments, radiation from a radionuclide is used to determine where the conjugate, such as the diagnostic conjugates described herein, is concentrated in a subject. Regardless of the method or device used, such detection is aimed at determining where the conjugate is concentrated in a subject, with such concentration being an indicator of the location of a tumor or tumor cells.

In some embodiments, the therapeutic conjugate is administered to a subject having cancer, e.g., an $\alpha_v\beta_6$ integrin-related cancer. Non-limiting examples of different types of cancer suitable for treatment using the therapeutic conjugates described herein include lung cancer, breast cancer, pancreatic cancer, bladder cancer, thyroid cancer, liver cancer, pleural cancer, ovarian cancer, cervical cancer, endometrial cancer, prostate cancer, testicular cancer, colon cancer, colorectal cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, skin cancer, oral squamous cell carcinoma, skin squamous cell carcinoma, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma. In certain embodiments, the cancer is lung cancer, breast cancer, colorectal cancer, pancreatic cancer, ovarian cancer, cervical cancer, oral squamous cell carcinoma, skin squamous cell carcinoma, stomach cancer, or endometrial cancer. In some cases, the subject has a primary lesion (e.g., a primary tumor). In some cases, the subject has a metastasis (e.g., a metastatic form of any of the cancer types described herein). In some cases, the subject has a primary lesion and a metastasis. In some embodiments, the subject has a pancreatic cancer such as locally advanced or metastatic pancreatic cancer, locally advanced, unresectable or metastatic pancreatic adenocarcinoma or pancreatic ductal adenocarcinoma (PDAC).

In some embodiments, the subject receives a dose of the therapeutic conjugate of Formula I containing between about 25 mCi and about 200 mCi radioactivity, such as a dose having about 25 mCi, about 50 mCi, about 100 mCi, about 150 mCi, or about 200 mCi radioactivity, administered over a period of minutes or hours, such as about 1 minute, about 2 minutes, about 5 minutes, about 10 minutes, about 15 minutes, about 20 minutes, about 25 minutes, about 30 minutes, about 35 minutes, about 40 minutes, about 45 minutes, about 55 minutes, about 1 hour, about 2 hours, about 3 hours, about 4 hours, about 5 hours, about 6 hours, about 7 hours, or about 8 hours. In certain embodiments, the subject receives a dose of the therapeutic conjugate of Formula I containing between about 25 mCi and about 200 mCi radioactivity, such as a dose having about 25 mCi, about 50 mCi, about 100 mCi, about 150 mCi, or about 200 mCi radioactivity, administered over a period of about 30 minutes.

In some embodiments, the subject receives a standard of care treatment prior to the administering of the dose of the therapeutic conjugate. In some aspects, the therapeutic conjugate has the structure of Formula I and the subject receives a dose of the therapeutic conjugate containing between about 25 mCi and about 200 mCi radioactivity, such as a dose having about 25 mCi, about 50 mCi, about 100 mCi, about 150 mCi, or about 200 mCi radioactivity, and prior to such dose, the subject receives a standard of care treatment. The standard of care treatment may comprise one or more of surgery, radiation therapy, chemotherapy, chemoradiation therapy and targeted therapy. The standard of care treatment may comprise FOLFIRINOX (leucovorin calcium (folinic acid), fluorouracil, irinotecan hydrochloride and oxaliplatin). The standard of care treatment may comprise gemcitabine, abraxane or a combination thereof. The standard of care treatment may comprise irinotecan. The standard of care may comprise surgery or surgery and one or more of FOLFIRINOX, gemcitabine, abraxane and irinotecan.

In some embodiments, the subject receives a standard of care treatment subsequent to the administering of the dose of the therapeutic conjugate. In some aspects, the therapeutic conjugate has the structure of Formula I and the subject receives a dose of the therapeutic conjugate containing between about 25 mCi and about 200 mCi radioactivity, such as a dose having about 25 mCi, about 50 mCi, about 100 mCi, about 150 mCi, or about 200 mCi radioactivity, and subsequent to such dose, the subject receives a standard of care treatment. The standard of care treatment may comprise one or more of surgery, radiation therapy, chemotherapy, chemoradiation therapy and targeted therapy. The standard of care treatment may comprise FOLFIRINOX (leucovorin calcium (folinic acid), fluorouracil, irinotecan hydrochloride and oxaliplatin). The standard of care treatment may comprise gemcitabine, abraxane or a combination thereof. The standard of care treatment may comprise irinotecan. The standard of care may comprise surgery or surgery and one or more of FOLFIRINOX, gemcitabine, abraxane and irinotecan.

In some embodiments, the subject receives one or more standard of care treatments prior to and subsequent to the administering of the dose of the therapeutic conjugate. In some aspects, the therapeutic conjugate has the structure of Formula I and the subject receives a dose of the therapeutic conjugate containing between about 25 mCi and about 200 mCi radioactivity, such as a dose having about 25 mCi, about 50 mCi, about 100 mCi, about 150 mCi, or about 200 mCi radioactivity, and both prior to and subsequent to such dose, the subject receives a standard of care treatment. The standard of care treatment may comprise one or more of surgery, radiation therapy, chemotherapy, chemoradiation therapy and targeted therapy. The standard of care treatment may comprise FOLFIRINOX (leucovorin calcium (folinic acid), fluorouracil, irinotecan hydrochloride and oxaliplatin). The standard of care treatment may comprise gemcitabine, abraxane or a combination thereof. The standard of care treatment may comprise irinotecan. The standard of care may comprise surgery or surgery and one or more of FOLFIRINOX, gemcitabine, abraxane and irinotecan. The standard of care prior to and subsequent to the treatment with the therapeutic conjugate may be the same. The standard of care prior to and subsequent to the treatment with the therapeutic conjugate may be different from each other.

In some embodiments, treatment with the therapeutic conjugate results in stable disease, partial remission or complete remission in the subject (e.g., the methods described herein comprise administering to the subject a dose of the therapeutic conjugate that kills or otherwise slows the growth or progression of cancer cells and leads to stable disease or to partial or complete remission of the cancer in the subject). In some embodiments, treatment with the therapeutic conjugate results in a reduction in metastases of the cancer in the subject (e.g., the methods described herein comprise administering to the subject a dose of the therapeutic conjugate that reduces metastases of the cancer in the subject). In some embodiments, treatment with the therapeutic conjugate results in a reduction in volume, size or growth of a tumor in the subject (e.g., the methods described herein comprise administering to the subject a dose of the therapeutic conjugate that reduces the volume, size or growth of a tumor in the subject). In some embodiments, treatment with the therapeutic conjugate results in an increased responsiveness of the cancer to a subsequently administered anti-cancer agent (e.g., the methods described herein comprise administering to the subject a dose of the therapeutic conjugate that increases responsiveness of the cancer to a subsequently administered anti-cancer agent).

In some embodiments, the subject is treated with the therapeutic conjugate of Formula I and the subject receives a dose of the therapeutic conjugate containing between about 25 mCi and about 200 mCi radioactivity, such as a dose having about 25 mCi, about 50 mCi, about 100 mCi, about 150 mCi, or about 200 mCi radioactivity, and the treatment with the therapeutic conjugate results in stable disease, partial remission or complete remission in the subject (e.g., the dose of the therapeutic conjugate kills or otherwise slows the growth or progression of cancer cells and leads to stable disease or to partial or complete remission of the cancer in the subject).

In some embodiments, the subject is treated with the therapeutic conjugate of Formula I and the subject receives a dose of the therapeutic conjugate containing between about 25 mCi and about 200 mCi radioactivity, such as a dose having about 25 mCi, about 50 mCi, about 100 mCi, about 150 mCi, or about 200 mCi radioactivity, and the treatment with the therapeutic conjugate results in a reduction in metastases of the cancer in the subject (e.g., the dose of the therapeutic conjugate reduces metastases of the cancer in the subject).

In some embodiments, the subject is treated with the therapeutic conjugate of Formula I and the subject receives a dose of the therapeutic conjugate containing between about 25 mCi and about 200 mCi radioactivity, such as a dose having about 25 mCi, about 50 mCi, about 100 mCi, about 150 mCi, or about 200 mCi radioactivity, and the treatment with the therapeutic conjugate results in a reduction in volume, size or growth of a tumor in the subject (e.g., the dose of the therapeutic conjugate reduces the volume, size or growth of a tumor in the subject).

In some embodiments, the subject is treated with the therapeutic conjugate of Formula I and the subject receives a dose of the therapeutic conjugate containing between about 25 mCi and about 200 mCi radioactivity, such as a dose having about 25 mCi, about 50 mCi, about 100 mCi, about 150 mCi, or about 200 mCi radioactivity, and the treatment with the therapeutic conjugate results in an increased responsiveness of the cancer to a subsequently administered anti-cancer agent (e.g., the dose of the therapeutic conjugate increases responsiveness of the cancer to a subsequently administered anti-cancer agent).

In some embodiments, the subject has a pancreatic cancer, such as locally advanced, unresectable or metastatic pancreatic adenocarcinoma and the subject is treated with the therapeutic conjugate of Formula I and the subject receives a dose of the therapeutic conjugate containing between about 25 mCi and about 200 mCi radioactivity, such as a dose having about 25 mCi, about 50 mCi, about 100 mCi, about 150 mCi, or about 200 mCi radioactivity. In some aspects, the treatment results in stable disease, partial remission or complete remission in the subject (e.g., the dose of the therapeutic conjugate kills or otherwise slows the growth or progression of cancer cells and leads to stable disease or to partial or complete remission of the cancer in the subject). In some aspects, the treatment results in a reduction in metastases of the pancreatic cancer in the subject (e.g., the dose of the therapeutic conjugate reduces metastases of the cancer in the subject). In some aspects, the treatment results in a reduction in volume, size or growth of a pancreatic tumor in the subject (e.g., the dose of the therapeutic conjugate reduces the volume, size or growth of a tumor in the subject). In some aspects, the treatment results in an increased responsiveness of the cancer to a subsequently administered anti-cancer agent, such as a chemotherapeutic agent or a combination thereof (e.g., the dose of the therapeutic conjugate increases responsiveness of the cancer to a subsequently administered anti-cancer agent). In some aspects, the treatment results in an increased responsiveness of the cancer to a subsequently administered anti-cancer agent, such as FOLFIRINOX, gemcitabine, abraxane, irinotecan, or any combination thereof.

V. Pharmaceutical Compositions

The therapeutic and diagnostic conjugates described herein may be formulated as pharmaceutical compositions for use. Such pharmaceutical compositions may include the conjugate and one or more pharmaceutically-acceptable excipients suitable for injection and/or infusion.

The conjugates herein may be formulated as compositions for administration in the form of a liquid. The liquid can be useful for delivery by injection, such as intratumoral injection, or intravenous infusion. In a composition for administration by injection, one or more of a surfactant, preservative, wetting agent, dispersing agent, suspending agent, buffer, stabilizer (e.g., radioprotectant), and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben;

antioxidants such as ascorbic acid or sodium bisulfite; chelating agents such as ethylenediaminetetraacetic acid; buffers such as amino acids, acetates, citrates or phosphates; detergents, such as nonionic surfactants, polyols; and agents for the adjustment of tonicity such as sodium chloride or dextrose. The liquid compositions may include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants.

The compositions for administration herein are preferably sterile. The prevention of the action of microorganisms can be brought about by various antibacterial and antifungal agents, for example, parabens, chlorobutanol, phenol, sorbic acid and thimerosal.

The compositions for administration of the conjugates herein generally comprise at least one excipient, such as for instance water for infusion, physiologic salt solution (0.9% NaCl), or a cell buffer, preferably consisting of a physiologic salt solution substituted with a protein component such as human serum albumin (HSA).

Compositions of the conjugates for administration can be enclosed in ampoule, a disposable syringe or a multiple-dose vial made of glass, plastic or other material.

In some cases, the diagnostic conjugate is formulated in 0.9% sodium chloride solution, USP with ≤10% v/v ethanol absolute. In some cases, the therapeutic conjugate is formulated in 5 mg/mL sodium ascorbate, USP in 0.9% sodium chloride solution, USP with ≤10% v/v ethanol absolute.

VI. Examples

The following examples are offered to illustrate, but not to limit, the claimed subject matter.

Example 1: Therapeutic/Diagnostic Agents

The synthesis of DOTA-5G (Formula II) and DOTA-ABM-5G (Formula I) was performed on solid phase as previously described for NOTA-K(ABM)-$\alpha_v\beta_6$-BP using DOTA-tris(tert-butyl ester) as the chelator, as disclosed in Hausner et al. "The Effects of an Albumin Binding Moiety on the Targeting and Pharmacokinetics of an Integrin alphavbeta6-Selective Peptide Labeled with Aluminum [(18)F]Fluoride", Mol Imaging Biol 22, 1543-1552 (2020) ("Hausner 2020"), which is incorporated herein by reference in its entirety. Following removal of the N-terminal Fmoc protecting group from the fully protected peptide (NovaBiochem) 5G ($5G=PEG_{28}$-GNGVPNLRGDLQVLGQRVGRT-PEG28-NH2), (1 equiv) using 20% piperidine (v/v in DMF), the DOTA-tris (tert-butyl ester) (CheMatech) (3 equiv) was coupled using 1-[bis(dimethylamino)methylene]-1H-1,2,3-triazolo[4,5-b] pyridinium 3-oxide hexafluorophosphate (HATU) (2.8 equiv) and diisopropylethylamine (DIPEA) base (6 equiv) in dimethylformamide (DMF). The protecting groups were removed and DOTA-$\alpha_v\beta_6$-BP was cleaved from the resin using trifluoroacetic acid (TFA)/ethanedithiol/water/triisopropylsilane (94:2.5:2.5:1 v/v/v/v) at ambient temperature for 3 h. Pure product was isolated using RP-HPLC (Beckman Coulter Gold HPLC) and characterized by matrix-assisted laser desorption/ionization (MALDI) mass spectrometry (Bruker): DOTA-5G, HPLC retention time ($R_1$)=14.45 min; MALDI m/z=5198.2, Calculated=5199.1 [M+H]. DOTA-ABM-5G, HPLC $R_t$=17.07 min; MALDI m/z analysis=5786.1046, Calculated=M ($C_{251}H_{457}IN_{44}O_{98}$) 5783.1174, 5784.1252 $[M+H]^+$.

[$^{68}$Ga]Ga DOTA-5G and [$^{177}$Lu]Lu DOTA-ABM-5G were radiolabeled under cGMP conditions. The final product (Formula II) of [$^{68}$Ga]Ga DOTA-5G (≤100 μg peptide mass) contained approximately 185 MBq (5 mCi) radioactivity. $^{68}$Ga was eluted from a $^{68}$Ge/$^{68}$Ga generator (Eckert and Ziegler) using 5 mL of 0.1 N HCl and used without further purification. Radiolabeling was conducted at pH 4 in 1M HEPES buffer. DOTA-5G (45 μg) or DOTA-ABM-5G (50 μg) was mixed with $^{68}GaCl_3$ (4.3 mCi) in the reaction vessel. The mixture was heated at 90° C. for 15 min and injected on to the HPLC and purified product peak was collected, diluted in 15 mL water and loaded on to a C-18 SepPak light cartridge. The cartridge was washed with water and the final product eluted with 1.5 mL EtOH. This final product was then dried under a stream of nitrogen gas at 50° C., and formulated in PBS for use. The pure products were characterized by radio-HPLC, [$^{68}$Ga]Ga DOTA-5G co-eluted with the cold standard at 9.13 min. and [$^{68}$Ga]Ga DOTA-ABM-5G at 9.6 min.

Radiolabeling of peptides DOTA-5G and DOTA-ABM-5G with $^{177}$Lu was conducted at pH 5 in 0.1 M sodium acetate buffer by adding DOTA-5G (52 μg) or DOTA-ABM-5G (58 μg) to $^{177}LuCl_3$ (5 mCi) in 100-150 μL buffer and 25 μL of ascorbic acid (5 mg/mL). The reaction vessel and heated at 95° C. for 15 min. The radiochemical purity was monitored by i-TLC (TEC-control/BIODEX, solvent phase: 0.1M trisodium citrate), and the radio-HPLC method described above. The products were characterized by radio-HPLC, [$^{177}$Lu]Lu DOTA-5G co-eluted with the cold standard at 16.39 min. and [$^{177}$Lu]Lu DOTA-ABM-5G at 17.82 min., and the final product was formulated in PBS for use.

[$^{68}$Ga]Ga DOTA-5G and [$^{68}$Ga]Ga DOTA-ABM-5G were obtained in ≤98% radiochemical purity (RCP) after semi preparative HPLC purification. The molar activity at the start of the reaction was 0.5 Ci/μmol for both reactions. [$^{177}$Lu]Lu DOTA-5G and [$^{177}$Lu]Lu DOTA-ABM-5G were obtained in ≥97% RCP. The specific activity of both reactions was 0.5 Ci/μmol.

The product was used within about 120 minutes after manufacturing. The final product (Formula I) of [$^{177}$Lu]Lu DOTA-ABM-5G (<100 μg peptide mass) contains approximately 925-7400 MBq (25-200 mCi) radioactivity, specifically generating doses with 25, 50, 100, 150 and 200 mCi total. The product was used within about 6 hours after manufacturing.

(Formula I)

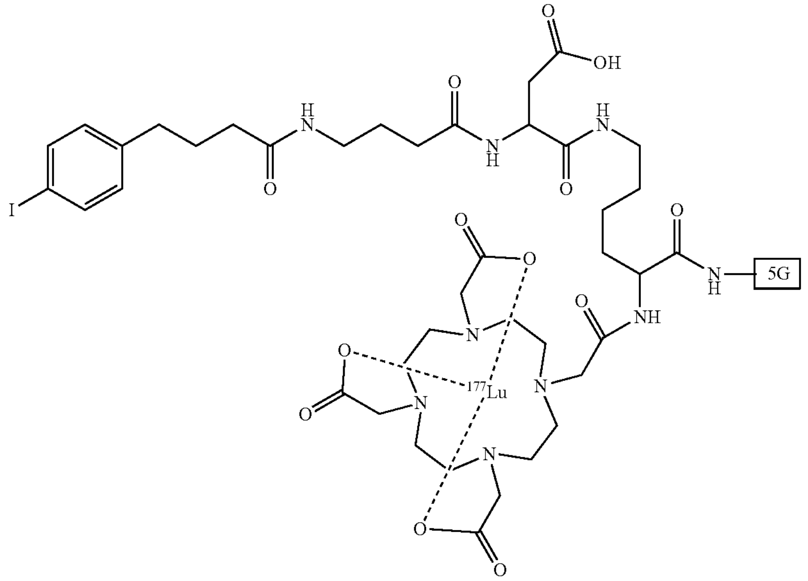

DOTA = 1,4,7,10-Tetraazacyclododecane-1,4,7,10-tetraacetic acid
ABM = K(D-Abu-iodophenylbutyryl) moiety
5G = $PEG_{28}$-GNGVPNLRGDLQVLGQRVGRT-$PEG_{28}$-$C(O)NH_2$ peptide Example 2: In Vitro $IC_{50}$ Determinations The 4-(p-iodophenyl)butyrate (IP) ABM was conveniently installed into peptide 1 using standard Fmoc-peptide chemistry. Competitive binding enzyme-linked immunosorbent assays (ELISAs) for integrins $\alpha_v\beta_6$ and $\alpha_v\beta_6$ followed previously described procedures as disclosed in Hausner et al. "Use of a peptide derived from foot-and-mouth disease virus for the noninvasive imaging of human cancer: Generation and evaluation of 4-[$^{18}$F]fluorobenzoyl A20FMDV2 for in vivo imaging of integrin alpha(v)beta(6) expression with positron emission tomography" Cancer Res. 2007; 67: 7833-40 ("Hausner 2007"), which is incorporated herein by reference in its entirety. Data was analyzed using Prism software (GraphPad Software, La Jolla, CA, USA)

Experiments were run in triplicate, using biotinylated latency-associated peptide (G&P Biosciences, Santa Clara, CA, USA) for $\alpha_v\beta_6$. Non-fat dry milk powder (Raley's, West Sacramento, CA, USA) was used in place of bovine serum albumin; Blocking Buffer consisted of PBS containing 0.5% milk powder (w/v) and 1% Tween 20 (v/v); Conjugate Buffer was prepared by adding 0.1% milk powder (w/v) to Wash Buffer as disclosed in Hausner 2007.

The binding affinities of DOTA-5G and DOTA-ABM-5G for integrin $\alpha_v\beta_6$, as determined by ELISA, were 35±1 nM and 27±4 nM, respectively (FIGS. 1A and 1B). As evident by the $IC_{50}$ values, this structural modification did not compromise the affinity of peptide 2 for the integrin $\alpha_v\beta_6$ (FIG. 2).

Example 3: In Vitro Cell Binding, Internalization and Efflux

Cell lines (ATCC) were analyzed with flow cytometry to confirm integrin expression levels. Binding of the radiotracers [$^{68}$Ga]Ga DOTA-5G and [$^{177}$Lu]Lu DOTA-ABM-5G to integrin $\alpha_v\beta_6$ and the internalization into BxPC-3 cells were determined at 60 min. post incubation as disclosed in Hu et al., "Characterization and Evaluation of $^{64}$Cu-Labeled A20FMDV2 Conjugates for Imaging the Integrin $\alpha_v\beta_6$", Mol Imaging Biol. 2014; 16: 567-77, which is incorporated herein by reference in its entirety.

Non-fat milk powder (0.5% wt/v in PBS) was used to pretreat the assay tubes to prevent non-specific binding. Samples from [$^{177}$Lu]Lu DOTA-ABM-5G were further analyzed to determine the efflux, post-internalization. The internalized fraction (pellet) was suspended in 0.3 mL of serum-free RPMI, the supernatant collected at 0.25 h and 1 h, respectively, and the pellet washed with another 0.3 mL of PBS. At each time point, the supernatants and wash were combined and the pellet was suspended in 0.6 mL PBS. The fraction of retained activity in the pellet was determined by the gamma counter.

All radiotracers showed $\alpha_v\beta_6$-targeted binding to and internalization into the cells at 1 h. For [$^{68}$Ga]Ga DOTA-5G, 9.7±1.0% (of total radioactivity) bound to the $\alpha_v\beta_6$(+) BxPC-3 cells, and 6.1±0.4% (of total radioactivity) internalized into the cells. For [$^{177}$Lu]Lu DOTA-ABM-5G, 29±1.4% (21.6±0.01% internalized) of the total activity was bound to the BxPC-3 cells (FIG. 1C), and negligible efflux (5%) was observed at 1 hour (FIG. 1D).

Example 4: In Vitro Albumin Binding

Binding of the radiotracers [$^{177}$Lu]Lu DOTA-5G and [$^{177}$Lu]Lu DOTA-ABM-5G to mouse and human serum proteins was evaluated by ultrafiltration using Centrifree Ultrafiltration devices (Millipore Sigma) according to the manufacturer's recommendations in quadruplicate as disclosed in Hausner 2020. The devices were pre-treated with PBS containing Tween 20 (5% v/v) as disclosed in Hausner 2007, followed by triplicate rinses with PBS. An aliquot of each formulated radiotracer in PBS (≤25 μL, 20-60 KBq) was thoroughly mixed with 0.5 mL serum at 37° C. in a microfuge tube. The mixture was incubated at 37° C. for 5 min and an aliquot (50 μL) of was transferred to a tube for γ-counting. The remaining sample was transferred to a Centrifree Ultrafiltration device and centrifuged for 40 min. at 1500×g at ambient temperature (20-24° C.). An aliquot (50 μL) of the filtrate was transferred to a tube for γ-counting. For each radiotracer, a blank was run using 0.5 mL PBS/Tween 20 (5% v/v) instead of serum (n=4) to determine non-specific binding. Following γ-counting, the protein-bound radioactivity was calculated by subtracting the counts measured in the filtrate aliquot (i.e., not protein bound) from the counts in the corresponding serum aliquot. The data are expressed as mean±standard deviation of fraction of radioactivity bound to protein after subtraction of non-specific binding determined in the blank.

Albumin binding determined by ultrafiltration for [$^{177}$Lu]Lu DOTA-ABM-5G was 54.4±2.8% and 58.1±0.4% for mouse and human serum, respectively, compared to 18.1±0.2% and 16.2±0.4%, respectively, for [$^{177}$Lu]Lu DOTA-5G.

Example 5: In Vitro Serum Stability

Mouse or human serum (500 μl, both purchased from Millipore Sigma) was combined with an aliquot of the formulated radiotracer (100-200 μCi) and incubated at 37° C. Aliquots (100-200 μl) were drawn for analysis at 1 and 2 h post-incubation for the $^{68}$Ga radiotracers and 1 and 24 h post-incubation for $^{177}$Lu radiotracers, mixed with absolute ethanol (500 μl, 4° C.), and centrifuged (2300× g, 3 min) to precipitate out serum proteins. The supernatant was diluted with HPLC Solvent A and analyzed by radio-HPLC to determine the fraction of intact radiotracer as disclosed in Hausner et al., "In vitro and in vivo evaluation of the effects of aluminum [$^{18}$F]fluoride radiolabeling on an integrin $\alpha_v\beta_6$-specific peptide" Nuclear medicine and biology. 2014; 41: 43-50, which is incorporated herein by reference in its entirety.

The stability of [$^{68}$Ga]Ga DOTA-5G, [$^{68}$Ga]Ga DOTA-ABM-5G, [$^{177}$Lu]Lu DOTA-5G, and [$^{177}$Lu]Lu DOTA-ABM-5G were investigated in both mouse and human serum. All radiotracers showed some degradation in mouse serum over time. In contrast, both [$^{68}$Ga]Ga DOTA-5G and [$^{68}$Ga]Ga DOTA-ABM-5G, were 100% stable at 2 h, and [$^{177}$Lu]Lu DOTA-5G and [$^{177}$Lu]Lu DOTA-ABM-5G were ≥97% stable at 24 h in human serum.

Example 6: In Vivo Imaging and Biodistribution

Female nu/nu nude mice (6-8 weeks old) were purchased from Charles River Laboratories (Wilmington, MA, USA) and handled according to the UC Davis Institutional Animal Care and Use Committee. BxPC-3 cells (5×10$^{6}$) in 100 μl 1:1 GFR-Matrigel: serum-free RPMI were implanted subcutaneously into the left shoulder flank and allowed to grow for approximately 2 weeks (therapy study) and 3 weeks (0.5-1 cm in diameter, for imaging and biodistribution studies). All cells were evaluated with flow cytometry before injection to confirm integrin expression levels. Food and water were available ad libitum.

For small animal imaging, aliquots of the formulated radiotracer (7.4-9.25 MBq in 100 μl) in PBS solution (pH 7.2) were injected intravenously (i.v.) via a catheter into the tail vein of mice (n=3/time point/radiotracer) anesthetized with 2-3% isoflurane in medical grade oxygen. Animals were imaged two at a time, side by side in a feet-first prone position on the scanner bed. Anesthesia was maintained during the scan at 1.5-2.5% isoflurane in medical-grade oxygen. A static, single-frame 15 min. emission scan was acquired at 1 h, and a 30 min. scan at 2 h post-injection (p.i.) for mice injected with [$^{68}$Ga]Ga DOTA-5G. A static 30 min. scan was acquired at 2 h and a 60 min. scan at 4 h p.i. for mice injected with [$^{68}$ Ga]Ga DOTA-ABM-5G. 57 Cobalt transmission scans for attenuation correction and CT scans for anatomical reference were also acquired at each time point. Representative images are shown in FIG. 2.

For biodistribution, aliquots of the formulated radiotracer (2.96-3.7 MBq in 100 p1 PBS) were injected into the tail vein followed by conscious uptake periods of 1 and 2 h ([$^{68}$ Ga]Ga DOTA-5G), 2 and 4 h ([$^{68}$ Ga]Ga DOTA-ABM-5G), and 1, 24, 48, and 72 h ([$^{177}$ Lu]Lu DOTA-5G and [$^{177}$ Lu]Lu DOTA-ABM-5G). For blocking studies, respective non-chelated cold peptide (30 mg/kg, 10 mg/mL (DOTA-5G) and 48 mg/kg, 16 mg/mL (DOTA-ABM-5G) solution in PBS) was injected 10 min. before the formulated radiotracer. At each time point, the mice (n=3/time point/radiotracer) were anesthetized and sacrificed. The tissues were collected, rinsed with PBS, and the radioactivity of each measured with a gamma counter. Radioactivity concentrations were calibrated, decay-corrected, and expressed as percent of injected dose per gram of tissue (% ID/g).

[$^{68}$ Ga]Ga DOTA-5G and [$^{68}$ Ga]Ga DOTA-ABM-5G were evaluated by in vivo imaging. [$^{68}$ Ga]Ga DOTA-5G, [$^{68}$ Ga]Ga DOTA-ABM-5G, [$^{177}$ Lu]Lu DOTA-5G and [$^{177}$Lu]Lu DOTA-ABM-5G were evaluated by biodistribution in the subcutaneous BxPC-3 tumor model. The imaging and biodistribution for [$^{68}$ Ga]Ga DOTA-5G was performed at 1 and 2 h post-injection (p.i.) and for [$^{68}$ Ga]Ga DOTA-ABM-5G at 2 and 4 h p.i. Uptake in the BxPC-3 tumor was evident at all time points for both radiotracers.

Figures 3A, 3B, 3C, 3D:
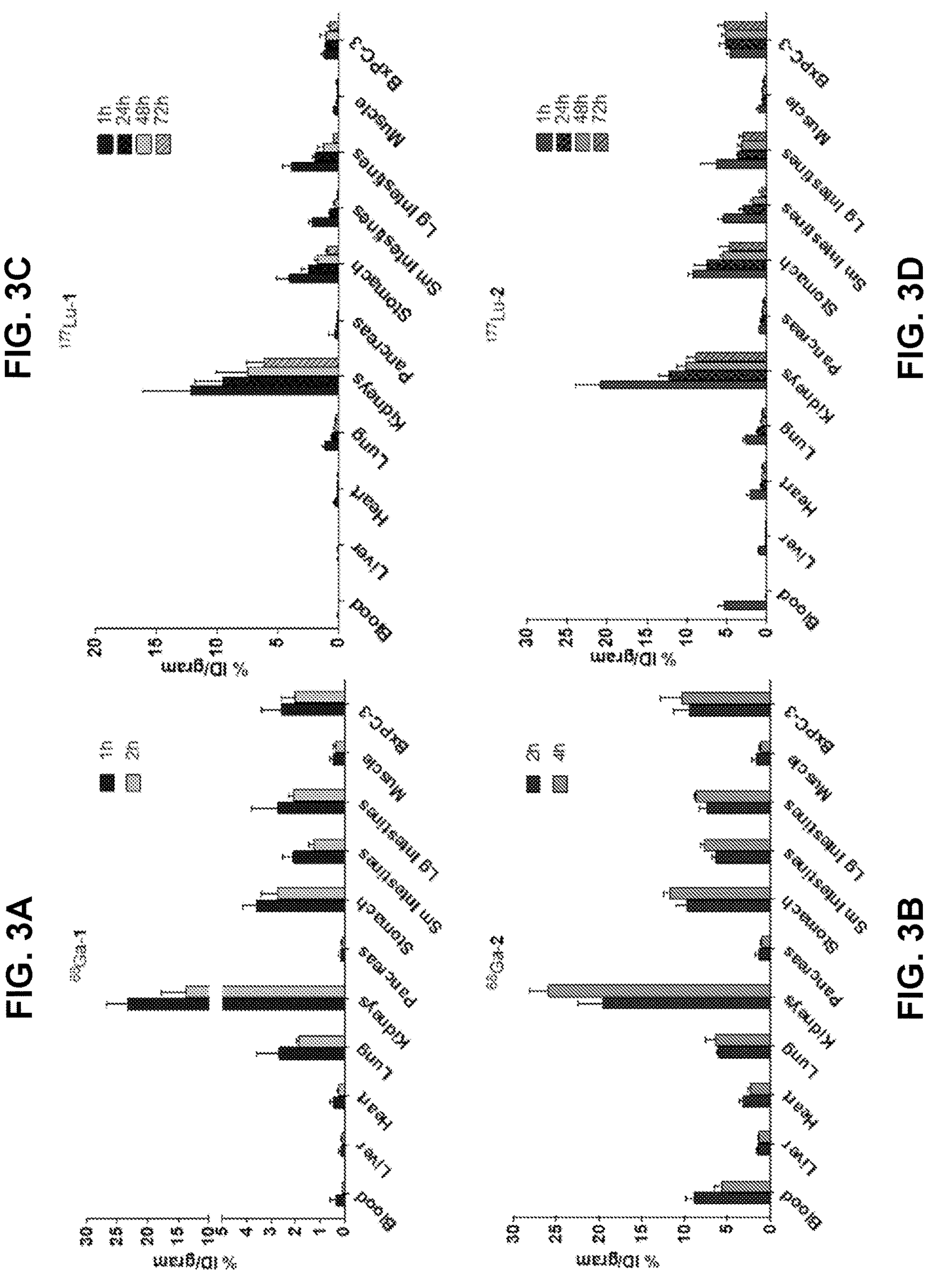
FIGS. 3A-3D show biodistribution of $^{68}$Ga-1 and $^{68}$Ga-2 (FIGS. 3A and 3B, respectively) and $^{177}$Lu-1 and $^{177}$Lu-2 (FIGS. 3C and 3D, respectively) shown in selected organs as percentage of decay corrected injected dose per gram of tissue in mice bearing $\alpha_v\beta_6$(+) BxPC-3 tumors (n=3/group/time point).

The uptake in the BxPC-3 tumor for [$^{68}$Ga]Ga DOTA-5G was 2.6±0.8% at 1 h and 2.03±0.6% at 2 h p.i.; and for [$^{68}$Ga]Ga DOTA-ABM-5G was 9.39±1.9% at 2 h and 10.35±2.6% at 4 h p.i. (FIGS. 3A and 3B). The difference in uptake between [$^{68}$Ga]Ga DOTA-5G and [$^{68}$Ga]Ga DOTA-ABM-5G is reflected in the PET/CT images (FIG. 2), where the uptake of [$^{68}$Ga]Ga DOTA-ABM-5G in the tumor appears significantly higher than [$^{68}$Ga]Ga DOTA-5G at 2 h p.i.

The kidney was the major route for elimination for both [$^{68}$Ga]Ga DOTA-5G and [$^{68}$Ga]Ga DOTA-ABM-5G. For [$^{68}$Ga]Ga DOTA-5G, the uptake at 1 h was 23.34±3.31% ID/g, and dropped to 13.83±3.91% ID/g at 2 h (p=0.032). For [$^{68}$Ga]Ga DOTA-ABM-5G, the uptake was 19.62±2.83% ID/g at 2 h, increasing to 25.92±2.24% ID/g at 4 h (p=0.039) (FIGS. 3A and 3B, Table 1). The BxPC-3/kidney ratio for [$^{68}$Ga]Ga DOTA-5G increased slightly from 0.12±0.05 (1 h) to 0.16±0.07 (2 h), and [$^{68}$ Ga]Ga DOTA-ABM-5G decreased slightly from 0.48±0.12 (2 h) to 0.41±0.13 (4 h) (both: p>0.05).

TABLE 1

| Biodistribution of [$^{68}$Ga]Ga DOTA-5G and [$^{68}$Ga]Ga DOTA-ABM-5G in mice bearing BxPC-3 ($\alpha_v\beta_6$ (+)) tumors (n = 3/group/time point). | | | | |
|---|---|---|---|---|
| | $^{68}$Ga-1 (% ID/g) | | $^{68}$Ga-2 (% ID/g) | |
| Tissue | 1 h | 2 h | 2 h | 4 h |
| Blood | 0.34 ± 0.27 | 0.09 ± 0.01 | 8.89 ± 0.89 | 5.72 ± 0.78 |
| Gall Bladder | 4.58 ± 7.02 | 0.49 ± 0.12 | 1.91 ± 1.10 | 2.70 ± 2.64 |
| Liver | 0.14 ± 0.09 | 0.11 ± 0.02 | 1.46 ± 0.16 | 1.36 ± 0.02 |
| Heart | 0.46 ± 0.12 | 0.27 ± 0.02 | 3.24 ± 0.35 | 2.28 ± 0.35 |
| Lung | 2.68 ± 0.91 | 1.87 ± 0.12 | 6.08 ± 0.11 | 6.41 ± 1.03 |
| Spleen | 0.07 ± 0.07 | 0.03 ± 0.00 | 1.10 ± 0.95 | 1.02 ± 0.11 |
| Kidneys | 23.34 ± 3.31 | 13.83 ± 3.91 | 19.62 ± 2.83 | 25.92 ± 2.24 |
| Pancreas | 0.17 ± 0.05 | 0.10 ± 0.02 | 1.37 ± 0.36 | 1.08 ± 0.12 |
| Stomach | 3.61 ± 0.55 | 2.75 ± 0.63 | 9.72 ± 1.29 | 11.80 ± 0.65 |
| Sm Intestines | 2.12 ± 0.42 | 1.27 ± 0.16 | 6.38 ± 0.43 | 7.70 ± 0.45 |
| Bladder | 36.23 ± 52.45 | 0.98 ± 0.4 | 7.81 ± 3.46 | 11.05 ± 11.19 |
| Skin | 0.93 ± 0.29 | 0.74 ± 0.25 | 4.10 ± 0.60 | 3.94 ± 0.78 |
| Muscle | 0.47 ± 0.14 | 0.34 ± 0.08 | 1.66 ± 0.44 | 1.15 ± 0.1 |
| Bone | 0.27 ± 0.04 | 0.45 ± 0.35 | 1.55 ± 0.33 | 0.93 ± 0.36 |
| Lg Intestines | 2.75 ± 1.04 | 2.08 ± 0.21 | 7.42 ± 0.83 | 8.73 ± 0.11 |
| Brain | 0.03 ± 0.01 | 0.02 ± 0.00 | 0.31 ± 0.02 | 0.18 ± 0.04 |
| BxPC-3 | 2.6 ± 0.8 | 2.03 ± 0.57 | 9.39 ± 1.89 | 10.35 ± 2.58 |

An increased circulation of [$^{68}$Ga]Ga DOTA-ABM-5G in blood was observed by PET imaging, as compared to [$^{68}$Ga]Ga DOTA-5G, especially at 2 h (FIGS. 3A and 3B). This was mirrored by the biodistribution results, where an 8-fold higher % ID/g was observed in blood at 2 h for [$^{68}$Ga]Ga DOTA-ABM-5G (8.89±0.89% ID/g), as compared to [$^{68}$Ga]Ga DOTA-5G (0.09±0.01% ID/g). The BxPC-3/blood ratio for [$^{68}$Ga]Ga DOTA-5G was 12.92±0.73 at 1 h, and increased to 22.05±3.86 at 2 h (p=0.0158). For [$^{68}$Ga]Ga DOTA-ABM-5G, the BxPC-3/blood ratio was 1.06±0.22 at 2 h, and 1.94±0.12 at 4 h (p=0.003).

The stomach and the intestines showed elevated levels of radioactivity for both [$^{68}$Ga]Ga DOTA-5G and [$^{68}$Ga]Ga DOTA-ABM-5G, with uptake in all organs being ≥4-fold for [$^{68}$Ga]Ga DOTA-ABM-5G as compared to [$^{68}$Ga]Ga DOTA-5G at 2 h p.i.; % ID/g—Stomach: 2.75±0.63 ([$^{68}$Ga]Ga DOTA-5G) and 11.8±0.65 ([$^{68}$Ga]Ga DOTA-ABM-5G), Small intestine: 1.27±0.16 ([$^{68}$Ga]Ga DOTA-5G) and 7.70±0.45 ([$^{68}$Ga]Ga DOTA-ABM-5G), Large intestine: 2.08±0.21 ([$^{68}$Ga]Ga DOTA-5G) and 8.73±0.11 ([$^{68}$Ga]Ga DOTA-ABM-5G) (FIGS. 3A and 3B, Table 1). The resultant BxPC-3/organ ratios at 2 h p.i. were BxPC-3/stomach: 0.75±0.23 ([$^{68}$Ga]Ga DOTA-5G) and 0.88±0.25 ([$^{68}$Ga]Ga DOTA-ABM-5G); BxPC-3/small intestine: 1.63±0.54 ([$^{68}$Ga]Ga DOTA-5G) and 1.34±0.31 ([$^{68}$Ga]Ga DOTA-ABM-5G); BxPC-3/large intestine: 0.98±0.26 ([$^{68}$Ga]Ga DOTA-5G) and 1.18±0.29 ([$^{68}$Ga]Ga DOTA-ABM-5G). The BxPC-3/liver ratio was 19.64±6.65 for [$^{68}$Ga]Ga DOTA-5G and 6.04±0.91 for [$^{68}$Ga]Ga DOTA-ABM-5G.

Figure 4A:
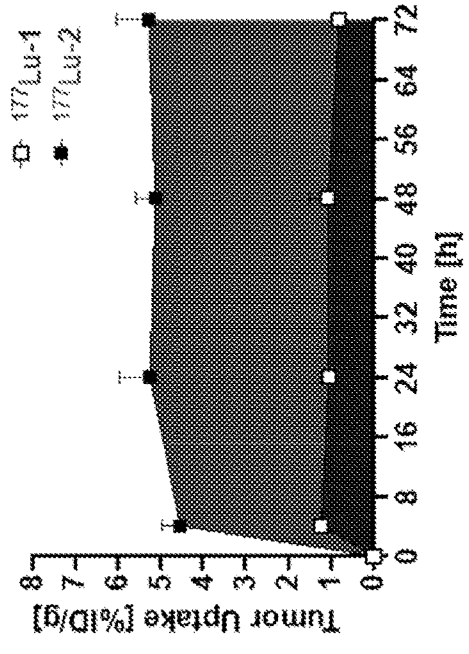
FIGS. 4A-4D show uptake of $^{177}$Lu-1 and $^{177}$Lu-2 in (FIG. 4A) BxPC-3 tumor, (FIG. 4B) kidney, (FIG. 4C) BxPC-3/kidney ratio and (FIG. 4D) BxPC-3/stomach ratio. Uptake values are expressed as percentage of decay corrected injected dose per gram (% ID/g) of tissue in mice bearing $\alpha_v\beta_6$ (+) BxPC-3 tumors (n=3/group/time point), derived from biodistribution data.

For the 177Lu labeled compounds, the uptake in the BxPc-3 tumor was at least 4-fold greater for [$^{177}$Lu]Lu DOTA-ABM-5G as compared to [$^{177}$Lu]Lu DOTA-5G at all times. Upon injection of [$^{177}$Lu]Lu DOTA-5G, the uptake in the tumor was 1.23±0.19% ID/g at 1 h showing slight washout over time, with 0.81±0.16% ID/g at 72 h (p=0.043). In contrast, the tumor uptake for [$^{177}$Lu]Lu DOTA-ABM-5G was 4.54±0.42% ID/g at 1 h, with retention up to 72 h (5.29±0.75% ID/g) (FIG. 4A).

Figure 4B:
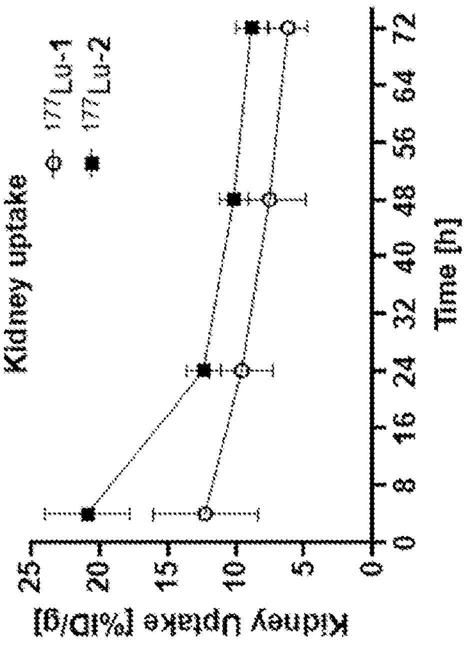
Figure 4C:
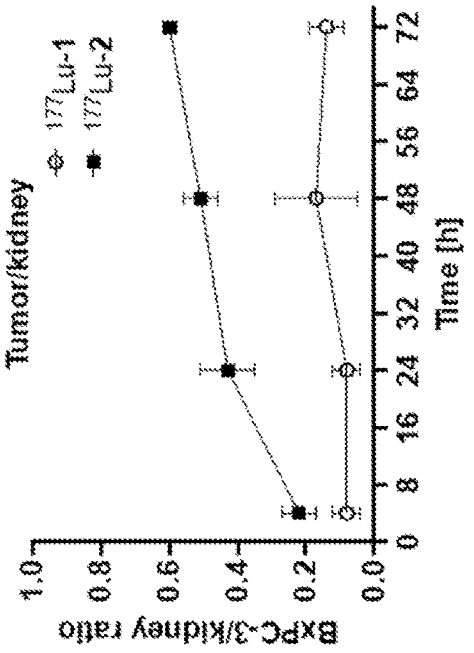

Both tracers showed uptake in the kidneys, with wash out over time. For [$^{177}$Lu]Lu DOTA-5G, the uptake was 12.23±3.91% ID/g at 1 h, and 6.16±1.45% ID/g at 72 h (p=0.0653). [$^{177}$Lu]Lu DOTA-ABM-5G also showed washout of activity over time, with an uptake of 20.89±3.1% ID/g at 1 h, and 8.84±1.15% ID/g at 72 h (p=0.0032) (FIG. 4B). The resulting BxPC-3/kidney uptake was 0.08±0.05 (1 h) and 0.14±0.05 (72 h) for [$^{177}$Lu]Lu DOTA-5G, and 0.22±0.05 (1 h) and 0.60±0.02 (72 h) for [$^{177}$Lu]Lu DOTA-ABM-5G (FIG. 4C).

An increased circulation of [$^{177}$Lu]Lu DOTA-ABM-5G in blood was observed due to the ABM, as was also evident in case of [$^{68}$Ga]Ga DOTA-ABM-5G. The % ID/g of [$^{177}$Lu]Lu DOTA-ABM-5G in blood was 5.36±0.71% ID/g at 1 h as compared to 0.10±0.02 for [$^{177}$Lu]Lu DOTA-5G. While [$^{177}$Lu]Lu DOTA-5G was undetectable in blood at later time points, [$^{177}$Lu]Lu DOTA-ABM-5G was still measurable at 72 h (0.01±0.00% ID/g) (Table 2 and Table 3).

TABLE 2

| Biodistribution of [$^{177}$Lu]Lu DOTA-5G in mice bearing BxPC-3 ($\alpha_v\beta_6$ (+)) tumors (n = 3/group/time point). | | | | |
|---|---|---|---|---|
| | $^{177}$Lu-1 (% ID/g) | | | |
| | 1 h | 24 h | 48 h | 72 h |
| Blood | 0.10 ± 0.03 | 0.00 ± 0.00 | 0.00 ± 0.00 | 0.00 ± 0.00 |
| Gall Bladder | 0.33 ± 0.29 | 0.18 ± 0.17 | 0.74 ± 0.97 | 0.34 ± 0.49 |
| Liver | 0.10 ± 0.03 | 0.06 ± 0.01 | 0.0 5 ± 0.00 | 0.04 ± 0.00 |
| Heart | 0.35 ± 0.04 | 0.14 ± 0.01 | 0.13 ± 0.03 | 0.10 ± 0.03 |
| Lung | 1.19 ± 0.18 | 0.53 ± 0.06 | 0.36 ± 0.09 | 0.27 ± 0.05 |
| Spleen | 0.03 ± 0.03 | 0.01 ± 0.01 | 0.01 ± 0.01 | 0.01 ± 0.01 |
| Kidneys | 12.23 ± 3.91 | 9.54 ± 2.33 | 7.52 ± 2.65 | 6.16 ± 1.45 |
| Pancreas | 0.41 ± 0.38 | 0.16 ± 0.03 | 0.13 ± 0.04 | 0.09 ± 0.00 |
| Stomach | 4.10 ± 0.98 | 2.55 ± 0.52 | 1.84 ± 0.08 | 0.95 ± 0.13 |
| Sm Intestines | 2.18 ± 0.33 | 0.82 ± 0.05 | 0.40 ± 0.06 | 0.13 ± 0.02 |
| Bladder | 3.83 ± 2.75 | 0.93 ± 0.29 | 0.89 ± 0.17 | 0.71 ± 0.24 |
| Skin | 0.75 ± 0.08 | 0.58 ± 0.09 | 0.41 ± 0.11 | 0.23 ± 0.06 |
| Muscle | 0.43 ± 0.05 | 0.18 ± 0.05 | 0.13 ± 0.01 | 0.11 ± 0.07 |
| Bone | 0.17 ± 0.13 | 0.11 ± 0.02 | 0.09 ± 0.02 | 0.06 ± 0.01 |
| Lg Intestines | 3.98 ± 0.62 | 1.95 ± 0.22 | 1.31 ± 0.4 | 0.46 ± 0.03 |
| Brain | 0.01 ± 0.00 | 0.01 ± 0.00 | 0.01 ± 0.00 | 0.01 ± 0.00 |
| BxPC-3 | 1.23 ± 0.19 | 1.05 ± 0.11 | 1.07 ± 0.45 | 0.81 ± 0.16 |

TABLE 3

| Biodistribution of [$^{177}$Lu]Lu DOTA-ABM-5G in mice bearing BxPC-3 ($\alpha_v\beta_6$ (+)) tumors (n = 3/group/time point). | | | | |
|---|---|---|---|---|
| | $^{177}$Lu-2 (% ID/g) | | | |
| | 1 h | 24 h | 48 h | 72 h |
| Blood | 5.36 ± 0.71 | 0.08 ± 0.01 | 0.02 ± 0.00 | 0.01 ± 0.00 |
| Gall Bladder | 1.72 ± 0.46 | 1.11 ± 0.71 | 0.71 ± 0.13 | 1.09 ± 0.61 |
| Liver | 1.05 ± 0.05 | 0.22 ± 0.01 | 0.16 ± 0.02 | 0.12 ± 0.01 |
| Heart | 2.05 ± 0.37 | 0.71 ± 0.05 | 0.64 ± 0.06 | 0.46 ± 0.11 |
| Lung | 2.68 ± 0.21 | 1.10 ± 0.15 | 0.68 ± 0.08 | 0.53 ± 0.10 |
| Spleen | 0.75 ± 0.03 | 0.12 ± 0.01 | 0.10 ± 0.02 | 0.10 ± 0.01 |
| Kidneys | 20.89 ± 3.10 | 12.34 ± 1.24 | 10.14 ± 1.04 | 8.84 ± 1.15 |
| Pancreas | 0.92 ± 0.07 | 0.60 ± 0.11 | 0.50 ± 0.09 | 0.36 ± 0.12 |
| Stomach | 9.16 ± 0.58 | 7.55 ± 1.45 | 5.49 ± 0.27 | 4.76 ± 1.22 |
| Sm Intestines | 5.46 ± 0.54 | 3.02 ± 0.32 | 1.74 ± 0.22 | 0.71 ± 0.16 |
| Bladder | 6.75 ± 2.39 | 2.91 ± 0.16 | 2.69 ± 0.33 | 3.29 ± 0.63 |
| Skin | 2.16 ± 0.35 | 1.49 ± 0.57 | 0.95 ± 0.05 | 1.08 ± 0.16 |
| Muscle | 0.96 ± 0.24 | 0.52 ± 0.08 | 0.52 ± 0.03 | 0.42 ± 0.02 |
| Bone | 0.66 ± 0.15 | 0.27 ± 0.08 | 0.16 ± 0.19 | 0.19 ± 0.13 |
| Lg Intestines | 6.31 ± 1.86 | 3.63 ± 0.09 | 3.13 ± 0.53 | 3.01 ± 0.44 |
| Brain | 0.14 ± 0.01 | 0.04 ± 0.01 | 0.02 ± 0.00 | 0.03 ± 0.00 |
| BxPC-3 | 4.54 ± 0.42 | 5.25 ± 0.71 | 5.12 ± 0.47 | 5.29 ± 0.75 |

Figure 4D:
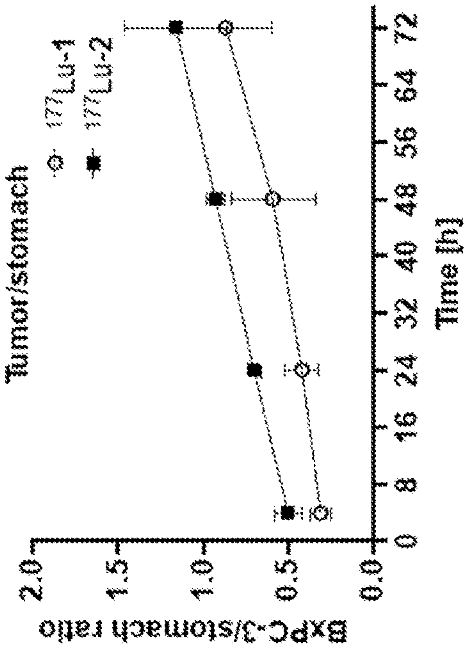

As seen in the case of [$^{68}$ Ga]Ga DOTA-5G and [68Ga]Ga DOTA-ABM-5G, an elevated uptake of both [$^{177}$Lu]Lu DOTA-5G and [$^{177}$Lu]Lu DOTA-ABM-5G was observed in the stomach, with wash out of activity over time; % ID/g for [$^{177}$Lu]Lu DOTA-5G—4.10±0.98 (1 h) and 0.95±0.13 (72 h) (p=0.0053), [$^{177}$Lu]Lu DOTA-ABM-5G—9.16±0.58 (1 h) and 4.76±1.22 (72 h) (p=0.0049). The resulting BxPC-3/stomach ratios were 0.31±0.06 (1 h) and 0.87±0.28 (72 h) for [$^{177}$Lu]Lu DOTA-5G and 0.50±0.08 (1 h) and 1.16±0.30 (72 h) for [$^{177}$Lu]Lu DOTA-ABM-5G (FIG. 4D). A similar trend of uptake was observed in the large intestines for both [$^{177}$Lu]Lu DOTA-5G and [$^{177}$Lu]Lu DOTA-ABM-5G, <4% ID/g for [$^{177}$Lu]Lu DOTA-5G and <7% ID/g for [$^{177}$Lu]Lu DOTA-ABM-5G at 4h, both dropping significantly over time (p=0.0006, [$^{177}$Lu]Lu DOTA-5G; p=0.0241, [$^{177}$Lu]Lu DOTA-ABM-5G—from 4 h-72 h). The BxPC-3/large intestine ratio was 0.31±0.02 (1 h) and 1.74±0.39 (72 h) for [$^{177}$Lu]Lu DOTA-5G and 0.77±0.25 (1 h) and 1.77±0.26 (72 h) for [$^{177}$Lu]Lu DOTA-ABM-5G. The uptake in the liver was <0.2% ID/g for [$^{177}$Lu]Lu DOTA-5G and <1% ID/g for [$^{177}$Lu]Lu DOTA-ABM-5G at 4 h, both dropping significantly over time.

Figure 5:
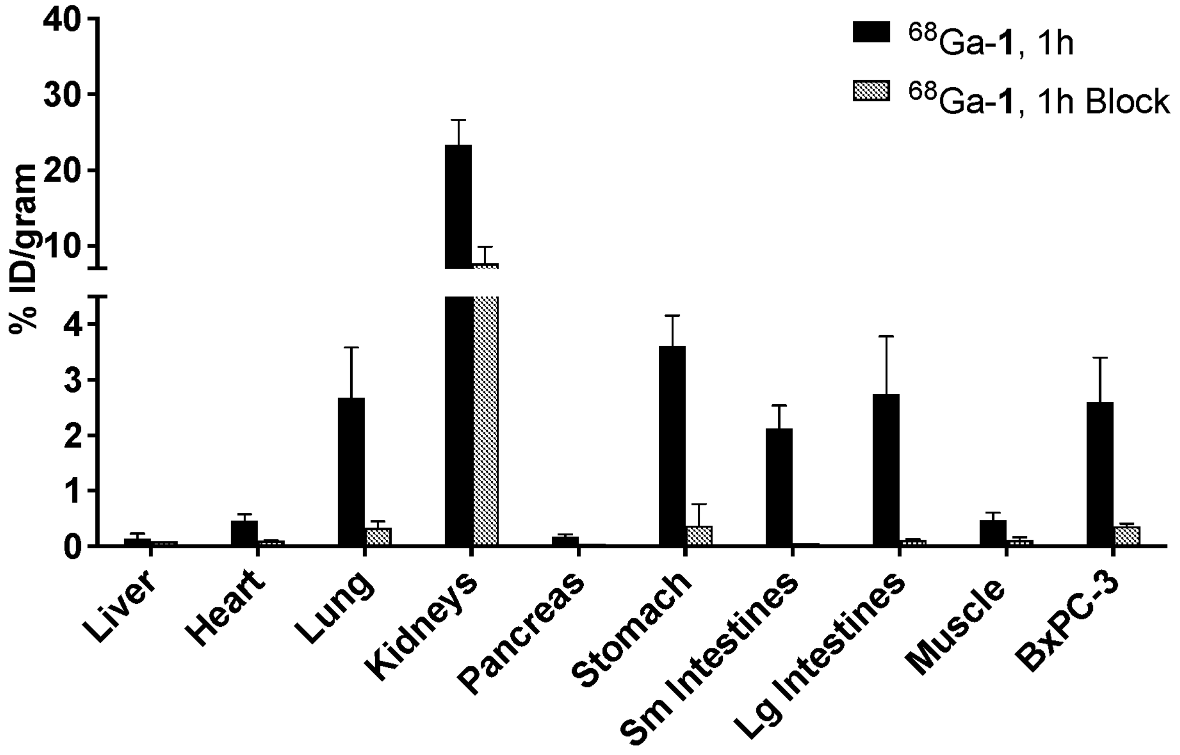
FIG. 5 shows biodistribution of $^{68}$Ga-1 as determined by radioactivity assays in mice bearing BxPC-3 ($\alpha_v\beta_6$ (+)) tumors at 1 hour post-injection (n=3/group). For blocking, 8.3 μmol/kg of 1 (30 mg/kg) was administered 10 minutes prior to the $^{68}$Ga-1 dose (n=2/group). Uptake data are expressed as decay-corrected percent of injected dose per gram of tissue (Columns: uptake [% ID/g]; bars: SD).
Figure 6:
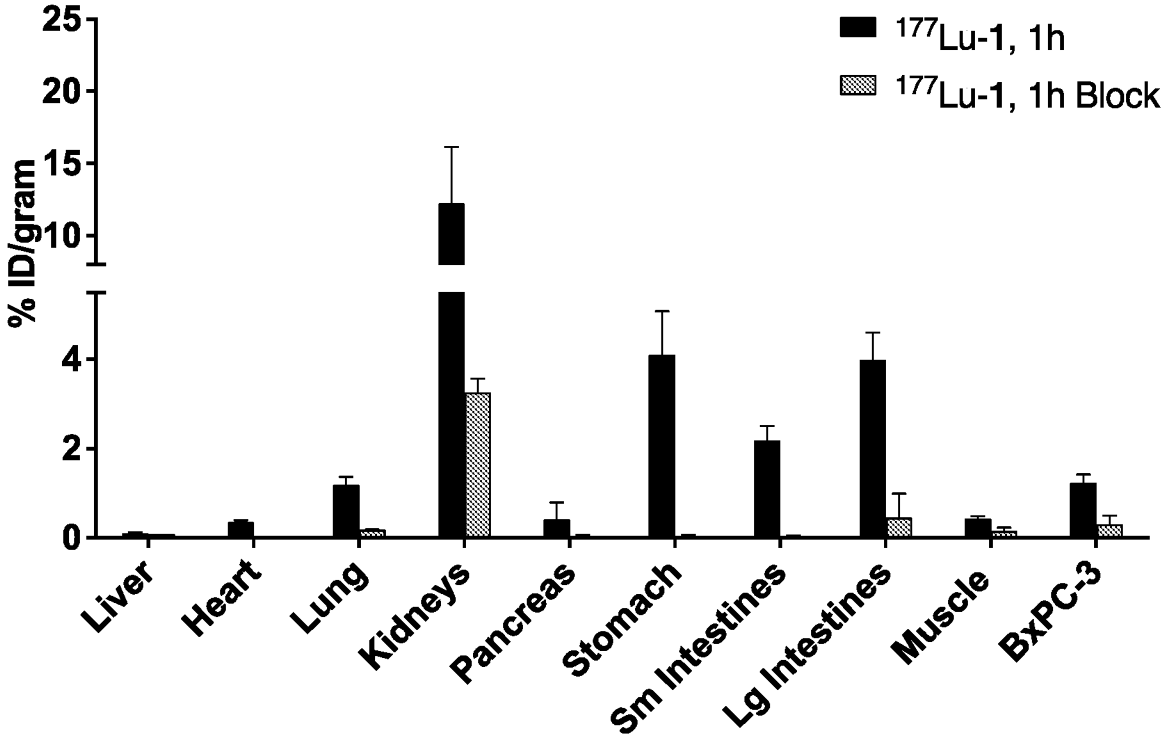
FIG. 6 shows biodistribution of $^{177}$Lu-1 as determined by radioactivity assays in mice bearing BxPC-3 ($\alpha_v\beta_6$ (+)) tumors at 1 hour post-injection (n=3/group). For blocking, 8.3 μmol/kg of 1(30 mg/kg) was administered 10 minutes prior to the 177 Lu-1 dose (n=2/group). Uptake data are expressed as decay-corrected percent of injected dose per gram of tissue (Columns: uptake [% ID/g]; bars: SD).
Figure 7:
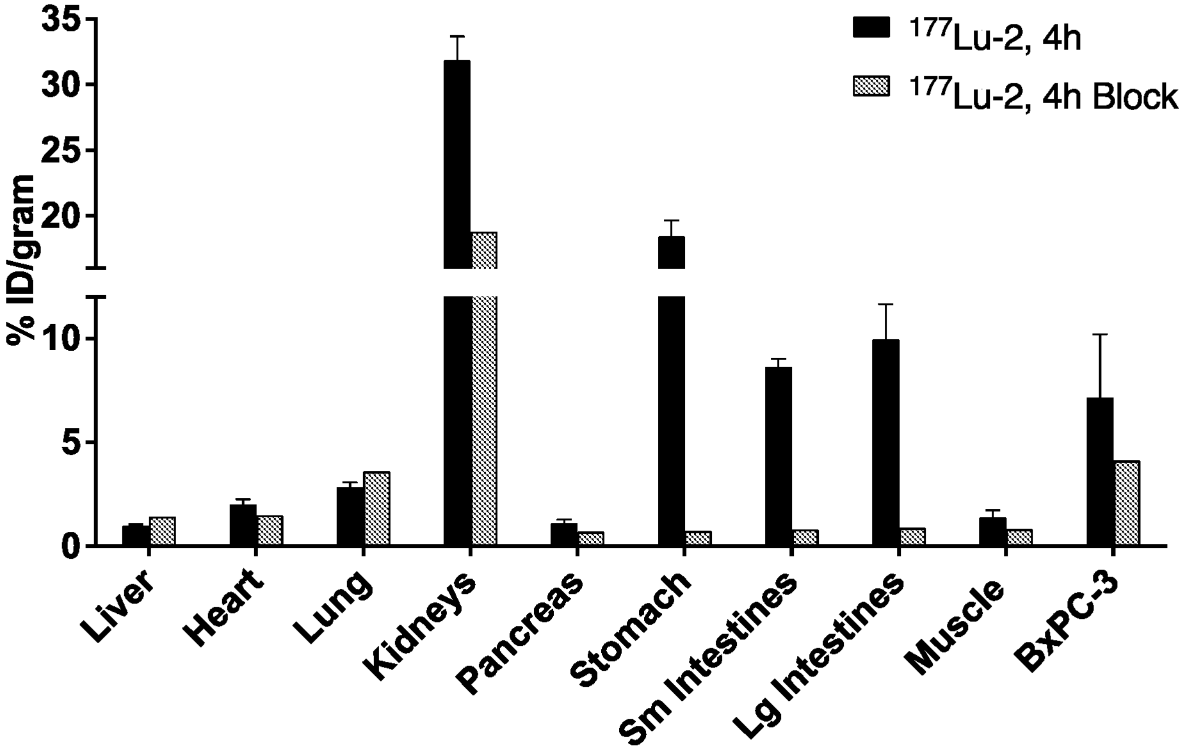
FIG. 7 shows biodistribution of $^{177}$Lu-2 as determined by radioactivity assays in mice bearing BxPC-3 ($\alpha_v\beta_6$ (+)) tumors at 4 hours post-injection (n=3/group). For blocking, 8.3 μmol/kg of 2 (48 mg/kg) was administered 10 minutes prior to the $^{177}$Lu-2 dose (n=1/group). Uptake data are expressed as decay-corrected percent of injected dose per gram of tissue (Columns: uptake [% ID/g]; bars: SD).

Pre-administration of the respective blocking peptide (DOTA-5G or DOTA-ABM-5G) 10 min. prior to administration of [$^{68}$Ga]Ga DOTA-5G, [$^{177}$Lu]Lu DOTA-5G and [$^{177}$Lu]Lu DOTA-ABM-5G resulted in reduction of uptake in the BxPC-3 tumor. The uptake reduced from 2.6±0.79% ID/g to 0.27±0.02% ID/g for [$^{68}$Ga]Ga DOTA-5G (Δ=−86%) and 1.23±0.19% ID/g to 0.3±0.02% ID/g for [$^{177}$Lu]Lu DOTA-5G (Δ=−75%), at 1 h p.i. For [$^{177}$Lu]Lu DOTA-ABM-5G, the uptake in the tumor reduced from 7.15±3.04% ID/g to 4.12% ID/g, 4 h p.i. (Δ=−42%) (FIGS. 5-7).

Example 7: In Vivo Targeted Radionuclide Therapy

For in vivo targeted radionuclide therapy, mice were implanted subcutaneously with BxPc-3 tumor cells 14 days before start of treatment. Mice were randomly chosen and divided into four treatment groups: Control Saline (Group 1, n=5); Control Peptide DOTA-ABM-5G (Group 2, n=6); 1×74 MBq [$^{177}$Lu]Lu DOTA-ABM-5G (Group 3, n=10); and 2×37 MBq [$^{177}$Lu]Lu DOTA-ABM-5G (Group 4, n=7). Average tumor volume at the start of the treatment was 14-218 mm$^3$. Group 2 received 20 μg of peptide DOTA-ABM-5G per mouse as a control. Group 3 received 74 MBq on day 14 post-tumor implant (treatment day 0), and Group 4 received two doses of 37 MBq on day 14 and 21 post-tumor implant (treatment days 0 and 7), at a specific activity of 18.5 MBq/nmol. Body weights and tumor volumes were measured the day before treatment, and twice a week post-treatment throughout the study. Tumor volume (TV) was determined according to the equation TV=(π/6)*L*W*H, where L is the longest axis, W is the axis perpendicular to L and H is perpendicular to the plane of L and W. End point determination was based on the longest axis of TV exceeding 2 cm, active ulceration, or compromised health of the mouse, including >20% loss of body weight from the start of the study. Survival curves are depicted as a Kaplan-Meier plot, using start of treatment as day 0.

Figure 9A:
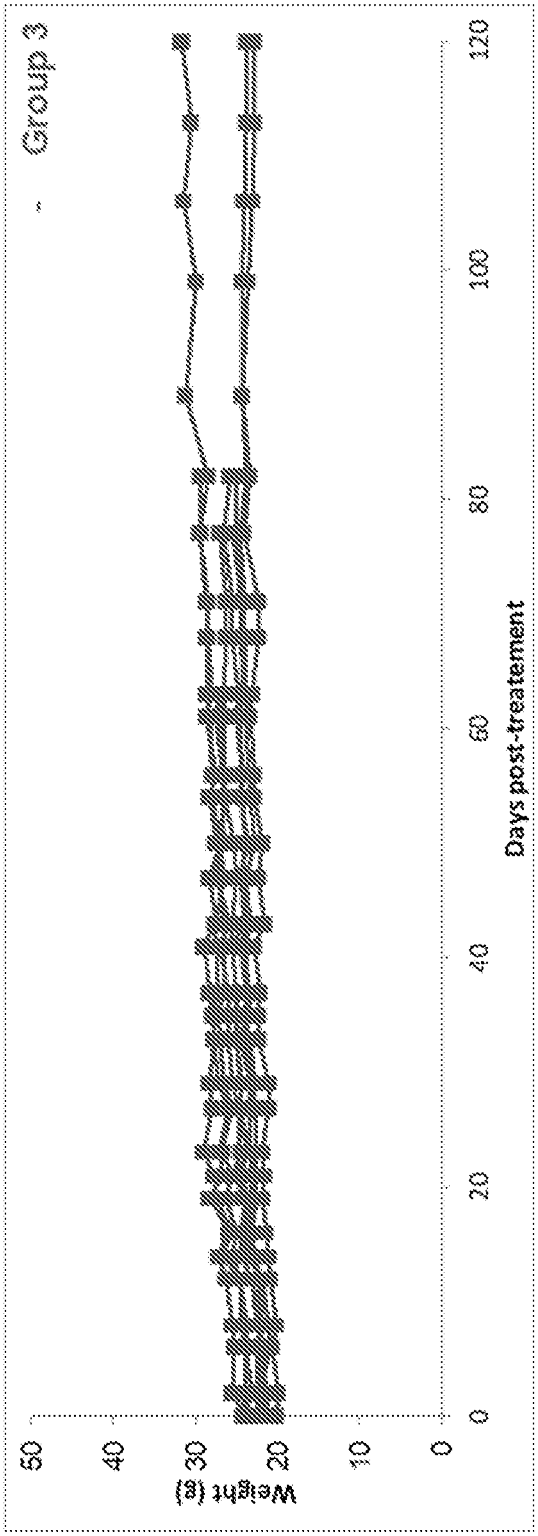
FIGS. 9A-9B show mouse weights which were measured twice per week until the end of study (120 days) for treatment groups 3 (FIG. 9A; 74 MBq $^{177}$Lu-2) and 4 (FIG. 9B; 2*37 MBq $^{177}$Lu-2).
Figure 9B:
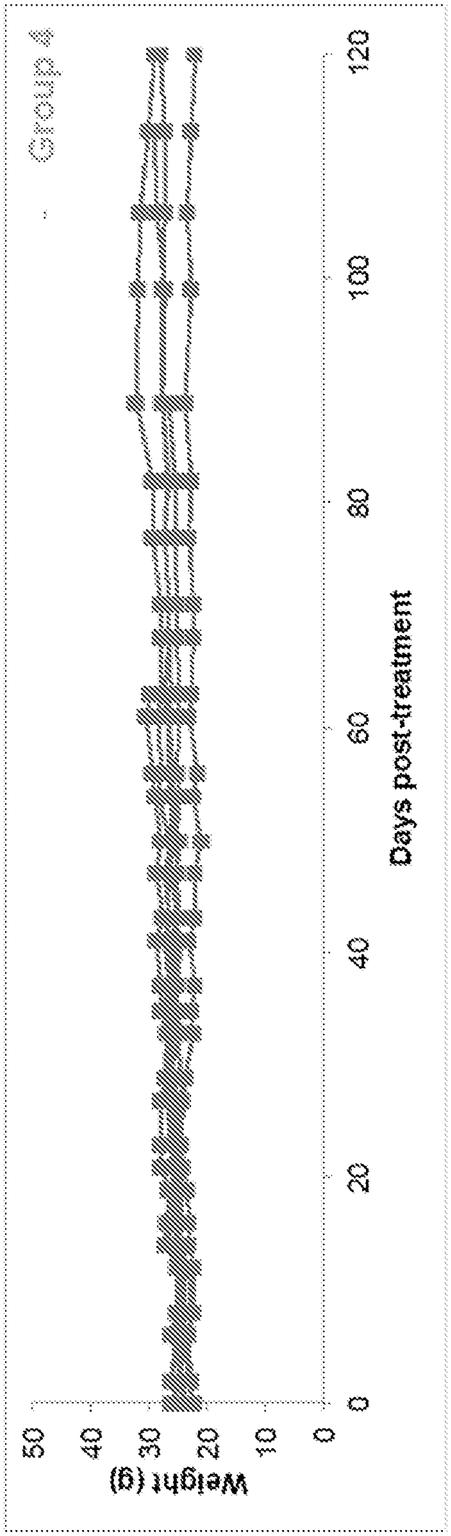
Figure 10:
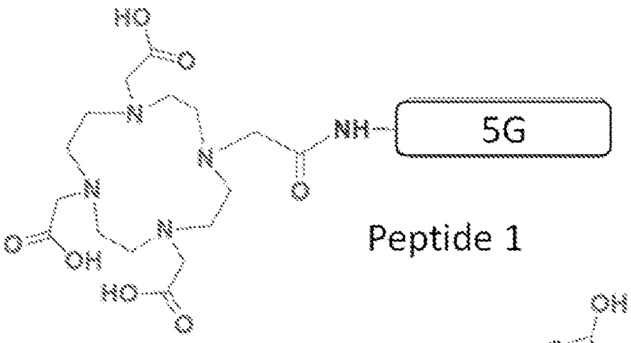
FIG. 10 shows peptide 1 which was used to create Formula II comprising peptide 1 with a $^{68}$Ga radionuclide (also referred to herein as [$^{68}$Ga]Ga DOTA-5G and $^{68}$Ga-1) and peptide 2 which was used to create Formula I comprising peptide 2 with a $^{177}$Lu radionuclide (also referred to herein as [$^{177}$Lu]Lu DOTA-ABM-5G and $^{177}$Lu-2). Peptide 1 was also used to create $^{177}$Lu-1 comprising peptide 1 with a $^{177}$Lu radionuclide. Peptide 2 was also used to create $^{68}$Ga-2 comprising peptide 2 with a $^{68}$Ga radionuclide.
Figure 10:
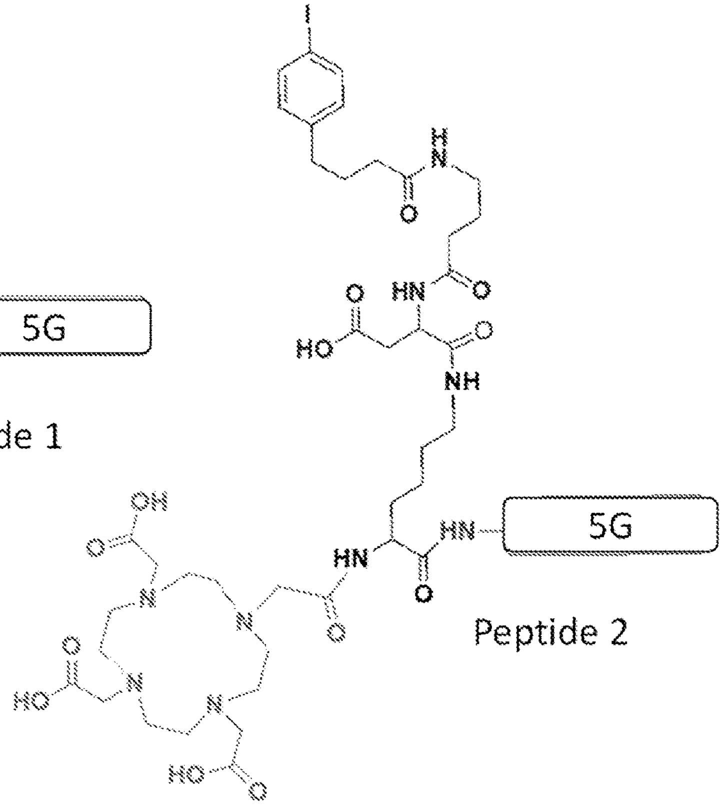

All mice in control Groups 1 (Saline control) and 2 (Peptide control) had met the end point criterion (≥2 cm in any direction and/or tumor ulceration) by 63 and 68 days from start of treatment, respectively. In contrast, the mice in Group 3 (74 MBq) and 4 (2×37 MBq) had a 30% and 43% survival rate, respectively, at the end of study (120 days). The median survival of mice post-treatment in each group was 56 days (Groups 1 and 2), 82 days (Group 3) and 113 days (Group 4) (FIG. 8B). No adverse events and weight loss was observed in any group during the course of the study (FIGS. 9A and 9B). Also, no adverse reaction to treatment was noted in the blood chemistry.

Example 8: Single Institution Pilot Study

A single institution pilot study was performed. Recruitment was open to all minorities and both genders.

Overview of Study Design/Intervention

Patients first underwent a single microdose of [$^{68}$Ga]Ga DOTA-5G PET/CT to assess eligibility for the [$^{177}$Lu]Lu DOTA-ABM-5G therapy. Only patients with sufficient lesion uptake (any visualized lesion with SUVmax>2-fold above normal lung or liver) were offered therapy with [$^{177}$Lu]Lu DOTA-ABM-5G. The study was designed as a 3+3 dose escalation study with [$^{177}$Lu]Lu DOTA-ABM-5G. The treatment regimen consisted of one dose of [$^{177}$Lu]Lu DOTA-ABM-5G. The 3+3 design included three patients for the first activity level group (25 mCi) (see Table 4, below). Dose-limiting toxicity (DLT) is defined as any treatment related AE≥grade 3 (G3). In addition, the radiation dose to the kidneys must not exceed 23 Gy and the dose to the bone marrow must not exceed 1.5 Gy. If no DLT occurs within 30 days (after the third patient), 3 patients were then enrolled at the next dose level. Should a patient not be available for complete evaluation of treatment related toxicity within the 30 day DLT window due to non-treatment related issues, the patient was replaced for the purpose of DLT assessment at the same dose level. If DLT attributable to the study treatment is experienced in exactly ⅓ subjects in the first course, 3 more patients (for a total of 6) are treated at that dose level. The dose was escalated if no additional DLT is observed at the expanded dose level (i.e., ⅙ with DLT). Escalation stops as soon as two or more subjects experience DLT attributable to the study drugs. The highest dose (200 mCi limit) with no more than one DLT out of six patients is recommended for Phase II. The radiation dose to the kidneys must not exceed 23 Gy and the dose to the bone marrow must not exceed 1.5 Gy. Table 4 shows the dose escalations for the study.

TABLE 4

Dose escalation of [$^{177}$Lu]Lu DOTA-ABM-5G.

| Dose Level | Administered dose of [$^{177}$Lu]Lu DOTA-ABM-5G |
|---|---|
| Dose Level 1 | 25 mCi |
| Dose Level 2 | 50 mCi |
| Dose Level 3 | 100 mCi |
| Dose Level 4 | 150 mCi |
| Dose Level 5 | 200 mCi |

Patients who meet entry criteria were enrolled by their treating oncologist or surgeon. All new patients were asked to complete a standard authorization for release of health information form, allowing investigators to request past laboratory and medical history information spanning the five years prior to the procedure from their referring or primary care physicians when it is applicable.

Inclusion Criteria

[$^{68}$Ga]Ga DOTA-5G PET/CT Inclusion Criteria:

1. Ability to understand and willingness to sign a written informed consent document.
2. Age 18 or more years
3. Confirmed presence of locally advanced, unresectable or metastatic pancreatic adenocarcinoma (other pancreatic malignant histologies are excluded) with measurable disease per RECIST (version 1.1) (i.e., at least 1 lesion>1 cm or lymph node>1.5 cm in short axis)
4. Participant must have documented tumor progression during or following at least one prior systemic regimen as established by CT or MRI scan within 28 days of enrollment
5. Eastern Cooperative Oncology Group Performance Status≤2
6. Participant must have completed prior chemotherapy at least 2 weeks (washout period) prior to [$^{68}$Ga]Ga DOTA-5G PET scan. Any clinically significant toxicity (with the exceptions of hair loss and sensory neuropathy) related to prior therapy resolved to Grade 1 or baseline.
7. Hematologic parameters defined as:
   a. Absolute neutrophil count (ANC)≥1000 cells/mm$^3$
   b. Platelet count≥100,000/mm$^3$
   c. Hemoglobin≥8 g/dL
8. Blood chemistry levels defined as:
   a. AST, ALT, alkaline phosphatase≤5 times upper limit of normal (ULN)
   b. Total bilirubin≤2 times ULN
   c. Creatinine≤2 times ULN
9. Anticipated life expectancy≥3 months
10. Able to remain motionless for up to 30-60 minutes per scan

[$^{177}$Lu]Lu DOTA-ABM-5G therapy Inclusion Criteria:

1. Completion of entry into [$^{68}$Ga]Ga DOTA-5G PET study and completion of scan
2. The presence of at least one measurable disease by [$^{68}$Ga]Ga DOTA-5G PET/CT (SUVmax>2-fold above normal lung or liver)

Exclusion Criteria

[$^{68}$Ga]Ga DOTA-5G and [$^{177}$Lu]Lu DOTA-ABM-5G therapy Exclusion Criteria:

1. Participant on therapeutic warfarin anticoagulation
2. Participants with Class 3 or 4 NYHA Congestive Heart Failure
3. Clinically significant bleeding within two weeks prior to trial entry (e.g., gastrointestinal bleeding, intracranial bleeding)
4. Pregnant or lactating women
5. Major surgery, defined as any surgical procedure that involves general anesthesia and a significant incision (i.e., larger than what is required for placement of a central venous access, percutaneous feeding tube, or biopsy) within 28 days prior to study day 1 or anticipated surgery within the subsequent 6 weeks
6. Has an additional active malignancy requiring therapy within the past 2 years
7. Active, uncontrolled bacterial, viral, or fungal infection(s) despite systemic therapy
8. Psychiatric illness/social situations that would interfere with compliance with study requirements
9. Prior external beam radiation therapy to more than 25% of the bone marrow
10. Cannot undergo PET/CT or SPECT/CT scanning because of weight limits (350 lbs)
11. INR>2.0; PTT>15 seconds above UNL Treatment of Subjects Pre-Treatment Evaluation Prior to treatment initiation, patients had an outpatient clinic visit which includes medical history, physical examination, vital signs, EKG, and ECOG assessment. Additionally, standard of care labs were obtained. These include liver function (ALT, AST, ALP, albumin, bilirubin), kidney function (creatinine and creatinine clearance), CBC (Hb, WBC count, platelet count). Blood samples for the exploratory outcomes to assess the $\alpha_v\beta_6$ levels in blood were drawn at baseline (exploratory). Patient demographics were taken including the sex, age, time since diagnosis and prior treatments.

Research Intervention

[$^{68}$Ga]Ga DOTA-5G PET/CT Studies.

Patients underwent [$^{68}$Ga]Ga DOTA-5G PET/CT scans to confirm eligibility for the [$^{177}$Lu]Lu DOTA-ABM-5G therapy. Prior to the [$^{68}$Ga]Ga DOTA-5G PET/CT, patients were encouraged to drink a sufficient amount of water necessary to urinate every hour on the day of infusion. There were no special fasting requirements. Up to 185 MBq (5 mCi) of [$^{68}$Ga]Ga DOTA-5G (Formula II, below) was injected IV as a bolus. Immediately after the injection, vital signs (heart rate, pulse oximetry value, body temperature, EKG) were measured. Patients were encouraged to void if possible. Patients then underwent scanning from the apex of the skull to the proximal thigh approximately 1 hour post injection of the [$^{68}$Ga]Ga DOTA-5G. 1 mL blood samples were obtained at serial time points throughout the uptake period (at approximately 5, 10, 15, 30, 60 minutes post injection) for time-activity-curve calculations. Vitals, blood samples and EKG were also checked 1 and 7 days (±48 hours) after injection of [$^{68}$Ga]Ga DOTA-5G for laboratory testing for full chemistry, hematology, and liver function tests.

(Formula II)

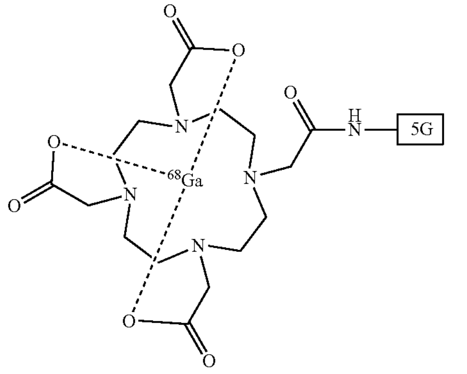

$^{68}$Ga = Gallium-68
DOTA = 1,4,7,10-Tetraazacyclododecane-1,4,7,10-tetraacetic acid
5G = $PEG_{28}$-GNGVPNLRGDLQVLGQRVGRT-$PEG_{28}$-C(O)$NH_2$ peptide

[$^{177}$Lu]Lu DOTA-ABM-5G Therapy Study.

Patients deemed eligible based on the [$^{68}$Ga]Ga DOTA-5GPET/CT were scheduled to receive one dose of the [$^{177}$Lu]Lu DOTA-ABM-5G therapy within 4 weeks (±7 days) of the [$^{68}$Ga]Ga DOTA-5G scan. Prior to the [$^{177}$Lu]Lu DOTA-ABM-5G administration, patients were encouraged to drink a sufficient amount of water necessary to urinate every hour on the day of infusion and the day after. Patients were encouraged to defecate every day for up to a week following the [$^{177}$Lu]Lu DOTA-ABM-5G treatment and to use laxative if needed. The doctor explains to the patient the general recommendations and precautions that should be followed to limit radiation exposure to third parties. For renal protection purpose, a 4-hour co-infusion of an amino acid solution (containing L-lysine [between 18 g and 24 g] and L-arginine [between 18 g and 24 g] was started 30 minutes prior to the infusion of [$^{177}$Lu]Lu DOTA-ABM-5G and continued at a constant rate (250 cc/hr) for a total of 4 hours. The patient was monitored for one hour after completion of the amino acid solution infusion. Administration of the amino acid solution before, during and after the [$^{177}$Lu]Lu DOTA-ABM-5G therapy was based on experience with Lu-177 DOTATATE to flush the radionuclide through the proximal tubules and decrease the radiation dose to the kidneys. To avoid treatment-related nausea and vomiting, antiemetic medications, including anti-H3 analogs (e.g., ondansetron), as per hospital procedure, were started 30 minutes before the start of the amino acid infusion. During the administration of amino acids and the following hours, the patient was encouraged to urinate as frequently as possible.

The biodistribution and dosimetry was evaluated using nuclear imaging at 1 day and 7 days post-infusion of [$^{177}$Lu]Lu DOTA-ABM-5G. Patients underwent whole body planar imaging (anterior and posterior view) and SPECT/CT (skull vertex extending through the perineum, terminating at the proximal thighs, approx. 2-4 bed positions) at approximately 24, and 168 hours following administration of [$^{177}$Lu]Lu DOTA-ABM-5G. In addition, serial blood samples were drawn at approximately 5, 15, 30, 60, 120 and 180 min following administration of [$^{177}$Lu]Lu DOTA-ABM-5G for evaluation of biodistribution. Full chemistry, hematology, liver function tests and EKG were performed at 1 day and 7 days (±48 hours).

Safety evaluation was evaluated by obtaining lab tests performed approximately every 2 weeks after the [$^{177}$Lu]Lu DOTA-ABM-5G infusion for up to 90 days to assess for possible delayed toxicities. These include: liver function (ALT, AST, ALP, albumin, bilirubin), kidney function (creatinine and creatinine clearance), hematology (Hb, WBC count, platelet count). The patients are followed until death or loss to follow-up to assess for possible late side effects from radiation therapy.

Exploratory studies of efficacy are determined by correlation with standard-of-care CT or MRI imaging for disease monitoring. We anticipate that this is obtained within 3 months following the [$^{177}$Lu]Lu DOTA-ABM-5G infusion.

This study is not anticipated to have any significant risks to the patient, however, safety is evaluated in this study through the monitoring of all serious and non-serious AEs, defined and graded according to NCI CTCAE V5.0. All patients are followed for AEs for 90 days. Patients who have an ongoing study treatment-related AE upon study completion or at discontinuation from the study are followed until the event has resolved to grade 1 or baseline grade (excluding hair loss, sensory neuropathy), the event is assessed by the investigator as stable, new anticancer treatment is initiated, the patient is lost to follow-up, the patient withdraws consent, or until it has been determined that study treatment or participation is not the cause of the AE.

Analyses of the Interventions

The ability of [$^{68}$Ga]Ga DOTA-5G to detect metastasis assessed by increased uptake (SUVmax>2-fold above normal lung or liver) of [$^{68}$Ga]Ga DOTA-5G in at least one metastasis assessed by [$^{68}$Ga]Ga DOTA-5G PET/CT is summarized as frequency, proportion, and exact 95% confidence interval for proportion.

Safety Analysis: Given that this is a first-in-human study, the main goal is to define safety and tolerability and characterize the AE profile. Safety, tolerability, and AEs are summarized using descriptive statistics. The AEs observed for [$^{68}$Ga]Ga DOTA-5G and [$^{177}$Lu]Lu DOTA-ABM-5G are summarized as frequency, proportion of patients, and exact 95% confidence interval for proportion, categorized by cohort, type and severity. Adverse events (AEs) are graded using Common Terminology Criteria for Adverse Events Version 5 (CTCAE). Dose-limiting toxicity is defined as any treatment related AE≥grade 3 (G3). For the [$^{68}$Ga]Ga DOTA-5G study, to assess changes in a given vital sign at days 1 and 7, paired t-tests are used to compare baseline to later time (using proper transformation if needed for normality). Population-averaged generalized estimating equation (GEE) are used to summarize trajectories of change for signs measured at multiple occasions. Diagnostic plots are used to identify potential outliers.

Efficacy Analysis: All responses are reported using RECIST 1.1 definitions. Response rate and 95% exact binomial confidence intervals are reported (exploratory).

Dosimetry Analysis: Descriptive statistics (mean, median, standard deviation, etc.) are reported for AUC based on activity concentration-time curves of [$^{177}$Lu]Lu DOTA-ABM-5G (separately for discernible thoracic and abdominal organs, target lesion, and blood), maximum uptake (achieved in %) at the target lesion and in discernible organs, specific absorbed dose per organ (μGy/MBq), and cumulative absorbed organ doses (Gy). Organs receiving the highest absorbed dose assessed by equivalent dose to tissue are tabulated using frequency and proportion. Graphic tools are also used to describe the endpoints.

Correlative Analysis (exploratory): Up to 5 lesions per patient that can be well identified on the SPECT/CT images of the dosimetry study are analyzed. For each tumor lesion, objective response to treatment is classified according to RECIST 1.1 criteria into binary outcome (response versus no response). We evaluate associations between response with following dosimetry measures: (i) [$^{68}$Ga]Ga DOTA-5G uptake (SUV), (ii) [$^{177}$Lu]Lu DOTA-ABM-5G uptake (Gy), (iii) difference between $\alpha_v\beta_6$ levels in blood pre and post [$^{177}$Lt]Lu DOTA-ABM-5G treatment, (iv) predictive value post-treatment $\alpha_v\beta_6$ levels in blood. Attempts to model associations between response with radiation doses are performed primarily using descriptive statistics; however, logistic mixed effects models may be used if warranted. In addition, the association between the safety parameters (e.g., CBC and CMP) and doses delivered to the organs are evaluated using descriptive statistics and mixed effects models. Proper transformation is applied to outcome if needed for normality (exploratory).

Radiologic Data

Radiologic data (from either CT or MRI though linked to each type of radiologic study) to be captured as part of patient entry include: location within the pancreas of the lesion, maximal size of the lesion, location of metastasis and size of metastasis.

PET/CT Imaging Data

The general distribution of [$^{68}$Ga]Ga DOTA-5G is determined by blood data and visual analysis of the scans. Reconstructed PET/CT images (skull apex to proximal-thigh whole body static) are displayed on the GE imaging workstation, reoriented into maximum intensity projection (MIP), transaxial, coronal and sagittal images. PET, fused PET/CT and CT images are all reviewed. Regions of interest (ROIs) are placed around tracer avid foci suspicious for malignancy and key organs (e.g., kidney, bladder, intestines, liver, spleen, lung, pancreas) in order to obtain SUV parameters, including SUVmax and SUV mean. All SUV measurements are summarized using mean, median, range, and counts where appropriate, and a repeated measures ANOVA model is used to relate the SUVs to the tissue regions. "Non-excreted" and "excreted" radioactivity are tracked. Non-excreted radioactivity in the body is calculated from volume-of-interest (VOI) analysis to derive the amount of radioactivity in major organs, tissues of interest and the remainder of the body. Data are scaled to the "Reference Man" anthropomorphic model for dosimetry purposes. Organ activity is integrated over time to get the time-integrated activity coefficient. OLINDA software is used to obtain dose and effective dose measurement.

SPECT/CT Imaging Data

The whole-body planar scan is used for qualitative evaluation of the [$^{177}$Lu]Lu DOTA-ABM-5G distribution. Radiation-absorbed doses to kidneys, stomach, uninvolved liver, bone marrow and whole body together with any other organs displaying [$^{177}$Lu]Lu DOTA-ABM-5G accumulation are calculated based on the analysis of serial blood counts and the SPECT/CT scans. The SPECT/CT study images are used to compute the volumetric absorbed radiation dose in the disease and healthy tissues. Specifically, activity concentration-time curves for normal tissues are generated from region-of-interest (ROI) analysis from the SPECT/CT scans. Activity concentration-time curves for red marrow and heart contents are generated from blood activity concentration measured by a well scintillation counter. Volumes of interest (VOI) are generated for each patient. It is assumed that the activity concentration in red bone marrow is equal to that in blood. Activity concentration-time curves are integrated (either analytically or numerically as appropriate) to yield AUC values from which so-called residence times are generated. These data are used as input to the FDA-approved dosimetry software package OLINDA/EXM 1.0, to generate absorbed dose estimates for normal tissues. The SPECT/CT acquisition and reconstruction study protocol follows the guidelines for Lu-tetium-177 SPECT-based dosimetry established by MIRD 26. The calibration of the SPECT/CT scanner is done using a uniform water phantom containing a calibrated Lu-177 source (e.g., 1 mCi). Supplementary dosimetry assessment includes lesion absorbed dose estimates based on image ROI analysis. Absorbed doses are normalized to administered activity and expressed in terms of mGy/MBq.

Blood Data (Exploratory)

Serum fluid from patients is collected and samples stored at −80° C. to avoid loss of bioactivity. The concentration of $\alpha_v\beta_6$ in serum is determined quantitatively with human ITGB6 enzyme-linked immunosorbent assay (ELISA) detection kit purchased by Cloud-Clone Corp (SEC099Hu, Texas, USA) following the manufacturer's instructions. The concentration in ng/mL is calculated and this data correlated to imaging and therapy data.

Dose Levels and Initial Patient Assessments

Patients from Dose Levels 1 and 2 were treated as described. Table 5 shows the prior treatment received by the patients and their status at enrollment. Radiation dose to the patients' kidneys and bone marrow are show in Table 5 as organ level internal dose assessment (OLINDA) and MRT. Initial status of the patients for the first two dose levels is shown in Table 6.

TABLE 5

| Patient # | Dose Level | Prior treatment | Status at enrollment | dose to kidneys OLINDA | dose to kidneys MRT | dose to bone marrow OLINDA | dose to bone marrow MRT |
|---|---|---|---|---|---|---|---|
| 1 | 1 | FOLFIRINOX, no surgery | large pancreas mass with progression to liver | 5.57 | 3.74 | 0.036 | 0 |
| 2 | 1 | Whipple, FOLFIRINOX, gem abraxane | progression to lungs | 4.14 | 3.07 | 0.027 | 0 |
| 3 | 1 | FOLFIRINOX, debulking surgery, gem abraxane | large pancreas mass, progression to lungs, liver, mesentery | 6.15 | 4.52 | 0.04 | 0 |
| 4 | 2 | FOLFIRINOX, no surgery, gem/abraxane | large pancreas mass, progression to lung and liver | 9.27 | 6.96 | 0.06 | 0.01 |

TABLE 5-continued

| Patient # | Dose Level | Prior treatment | Status at enrollment | dose to kidneys OLINDA | dose to kidneys MRT | dose to bone marrow OLINDA | dose to bone marrow MRT |
|---|---|---|---|---|---|---|---|
| 5 | 2 | FOLFIRINOX, distal pancreatectomy, gem abraxane, SBRT to liver lesion | progression to liver after SBRT | processing | processing | processing | processing |
| 6 | 2 | Distal pancreatectomy, FOLFIRINOX, gem abraxane | progression to liver and bone | processing | processing | processing | processing |

TABLE 6

| Patient # | Dose Level | Current treatment | Current status | Renal function over 90 days |
|---|---|---|---|---|
| 1 | 1 | none, hospice | alive, increase in metastatic burden | no change |
| 2 | 1 | resumed gem/abraxane | alive, stable disease | no change |
| 3 | 1 | none | Deceased (patient deteriorated quickly due to primary disease) | no change |
| 4 | 2 | irinotecan only | alive, no evidence of liver metastasis, reduction in size of lymph node | no change |
| 5 | 2 | pending review | alive | |
| 6 | 2 | will resume gem/abraxane | alive | |

VII. Exemplary Embodiments

Exemplary embodiments provided in accordance with the presently disclosed subject matter include, but are not limited to, the claims and the following embodiments:

1. A method of treating an $\alpha_v\beta_6$ integrin-related cancer comprising administering a dose of a therapeutic conjugate of Formula I to a subject in need of treatment (Formula I)

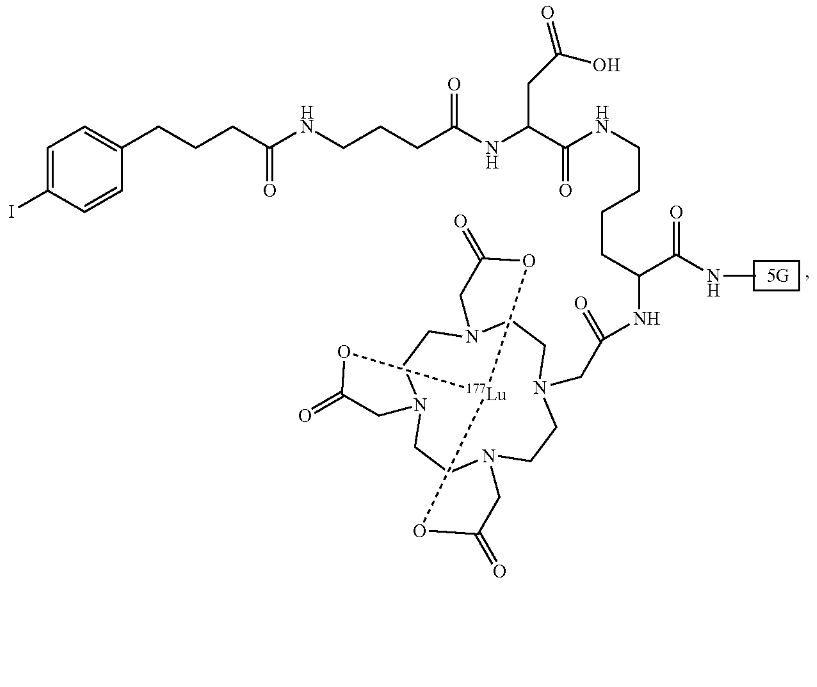

wherein 5G is a PEGylated peptide having the amino acid sequence GNGVPNLRGDLQVLGQRVGRT and comprising a first PEG moiety at the N-terminus of the peptide and a second PEG moiety at the C-terminus of the peptide, and wherein the dose of the therapeutic conjugate contains between about 25 mCi and about 200 mCi radioactivity.

2. The method of embodiment 1, wherein the first PEG moiety and the second PEG moiety each comprises PEG28 (PEG 1500).

3. The method of embodiment 1 or 2, wherein the amount of radioactivity in the dose is 25 mCi, 50 mCi, 100 mCi, 150 mCi, or 200 mCi.

4. The method of any one of embodiments 1-3, further comprising administering one, two, or three additional dose(s) of the therapeutic conjugate to the subject.

5. The method of any one of embodiments 1-4, wherein the dose includes no more than about 100 μg of the peptide.

6. The method of any one of embodiments 1-5, wherein the $\alpha_v\beta_6$ integrin-related cancer is pancreatic cancer, breast cancer, colorectal cancer, lung cancer, ovarian cancer, cervical cancer, oral squamous cell carcinoma, skin squamous cell carcinoma, stomach cancer, or endometrial cancer.

7. The method of embodiment 6, wherein the pancreatic cancer is locally advanced or metastatic pancreatic cancer; locally advanced, unresectable or metastatic pancreatic adenocarcinoma; or pancreatic ductal adenocarcinoma (PDAC).

8. The method of any one of embodiments 1-7, wherein the $\alpha_v\beta_6$ integrin-related cancer comprises a primary lesion and a metastatic lesion.

9. The method of any one of embodiments 1-8, wherein the $\alpha_v\beta_6$ integrin-related cancer comprises a lesion in an adrenal gland, bone, brain, liver, lung or any combination thereof.

10. The method of any one of embodiments 1-9, wherein the subject receives a standard of care treatment prior to the administering of the dose of the therapeutic conjugate.

11. The method of any one of embodiments 1-10, wherein the subject receives a standard of care treatment subsequent to the administering of the dose of the therapeutic conjugate.

12. The method of embodiment 10 or 11, wherein the standard of care treatment comprises one or more of surgery, radiation therapy, chemotherapy, chemoradiation therapy and targeted therapy.

13. The method of any one of embodiments 10-12, wherein the standard of care treatment comprises FOLFIRINOX (leucovorin calcium (folinic acid), fluorouracil, irinotecan hydrochloride and oxaliplatin), gemcitabine, abraxane, irinotecan, or a combination thereof.

14. The method of any one of embodiments 1-13, wherein the method further comprises scanning the body of the subject or a portion thereof after administering the therapeutic conjugate.

15. The method of embodiment 14, wherein the scanning comprises positron emission tomography (PET), computed tomography (CT) scanning, or single photon emission computerized tomography (SPECT).

16. The method of any one of embodiments 1-15, further comprising administering a diagnostic conjugate prior to the administration of the therapeutic conjugate, wherein the diagnostic conjugate comprises an RGD peptide and a second radionuclide.

17. The method of embodiment 16, wherein the second radionuclide is $^{68}$Ga.

18. The method of embodiment 16 or 17, wherein the diagnostic conjugate is administered in a dose that contains up to about 5 mCi radioactivity.

19. The method of any one of embodiments 16-18, wherein the method further comprises scanning the body of the subject or a portion thereof after administering the diagnostic conjugate.

20. The method of embodiment 19, wherein the scanning comprises positron emission tomography (PET), computed tomography (CT) scanning, or single photon emission computerized tomography (SPECT).

21. The method of any one of embodiments 16-20, wherein the therapeutic conjugate is administered within 5 weeks after the administration of the diagnostic conjugate.

22. The method of any one of embodiments 16-21, wherein the diagnostic conjugate comprises Formula II (Formula II)

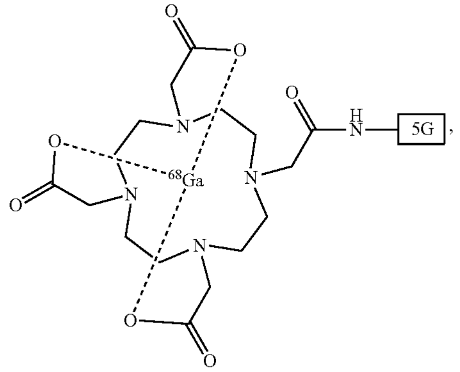

and wherein 5G is a PEGylated peptide having the amino acid sequence GNGVPNLRGDLQVLGQRVGRT and comprising a first PEG moiety at the N-terminus of the peptide and a second PEG moiety at the C-terminus of the peptide.

23. The method of embodiment 22, wherein the first PEG moiety and the second PEG moiety each comprises PEG28 (PEG 1500).

24. The method of any one of embodiments 1-23, further comprising administering a solution of amino acids to the subject.

25. The method of embodiment 24, wherein the solution is administered prior to and concurrent with the administration of the therapeutic conjugate.

26. The method of any one of embodiments 1-25, wherein the therapeutic conjugate is administered to the subject by infusion.

27. The method of any one of embodiments 16-26, wherein the diagnostic conjugate is administered to the subject by injection.

28. The method of any one of embodiments 1-27, wherein the treatment results in stable disease, partial remission or complete remission.

29. The method of any one of embodiments 1-28, wherein the treatment results in a reduction in metastases of the cancer in the subject.

30. The method of any one of embodiments 1-29, wherein the treatment results in a reduction in volume, size or growth of a tumor in the subject.

31. The method of any one of embodiments 1-30, wherein the treatment results in an increased responsiveness of the cancer to a subsequently administered anti-cancer agent.
32. The method of any one of embodiments 1-31, wherein the amount of the therapeutic conjugate that is present in kidney tissue at 24 hours, 48 hours or 72 hours after administration of the conjugate is lower than the amount of the therapeutic conjugate that is present in kidney tissue at one hour after administration of the conjugate.
33. The method of any one of embodiments 1-32, wherein the ratio of the amount of the therapeutic conjugate in a primary tumor to the amount of the therapeutic conjugate in kidney tissue at 24 hours, 48 hours or 72 hours after administration of the conjugate is higher than the ratio of the amount of the therapeutic conjugate in the primary tumor to the amount of the therapeutic conjugate in kidney tissue at 1 hour after administration of the conjugate.
34. A pharmaceutical composition comprising a peptide having the amino acid sequence GNGVPNLRGDLQVLGQRVGRT.
35. The pharmaceutical composition of embodiment 34, wherein a PEG moiety is covalently attached at the N-terminus, the C-terminus or both the N- and C-termini of the peptide.
36. The pharmaceutical composition of embodiment 35, wherein the PEG moiety is independently selected from the group consisting of PEG11, PEG12 (PEG 800), PEG28 (PEG 1500), and $(PEG28)_2$ (PEG 1500×2).
37. The pharmaceutical composition of embodiment 35, wherein a first PEG moiety is covalently attached to the N-terminus of the peptide and a second PEG moiety is covalently attached to the C-terminus of the peptide, and the first PEG moiety and the second PEG moiety are independently selected from the group consisting of PEG11, PEG12 (PEG 800), PEG28 (PEG 1500), and $(PEG28)_2$ (PEG 1500×2).
38. The pharmaceutical composition of embodiment 37, wherein the first PEG moiety and the second PEG moiety are the same.
39. The pharmaceutical composition of embodiment 38, wherein the first PEG moiety and the second PEG moiety each comprises PEG28 (PEG 1500).
40. The pharmaceutical composition of any one of embodiments 34-39, wherein the peptide is covalently attached to an albumin binding moiety (ABM).
41. The pharmaceutical composition of embodiment 40, wherein the ABM comprises 4-(4-iodophenyl)butyric acid.
42. The pharmaceutical composition of embodiment 40 or 41, wherein the ABM comprises a K(D-Abu-iodophenylbutyryl) moiety.
43. The pharmaceutical composition of any one of embodiments 34-42, wherein the peptide is covalently attached to a chelating moiety.
44. The pharmaceutical composition of embodiment 43, wherein the chelating moiety is DOTA.
45. The pharmaceutical composition of embodiment 43 or 44, wherein a radionuclide is complexed with the chelating moiety.
46. The pharmaceutical composition of any one of embodiments 34-45, wherein a radionuclide is covalently attached directly or indirectly to the peptide.
47. The pharmaceutical composition of embodiment 46, wherein the radionuclide is selected from the group consisting of $^{32}P$, $^{47}Sc$, $^{67}Cu$, $^{89}Sr$, $^{90}Y$, $^{105}Rh$, $^{111}Ag$, $^{117m}Sn$, $^{131}I$, $^{149}Pm$, $^{153}Sm$, $^{166}Ho$, $^{177}Lu$, $^{186}Re$, $^{188}Re$, $^{211}At$, and $^{212}Bi$.
48. The pharmaceutical composition of embodiment 46, wherein the radionuclide is selected from the group consisting of $^{11}C$, $^{13}N$, $^{15}O$, $^{18}F$, $^{55}Co$, $^{60}Cu$, $^{61}Cu$, $^{62}Cu$, $^{64}Cu$, $^{66}Ga$, $^{67}Cu$, $^{68}Ga$, $^{82}Rb$, $^{86}Y$, $^{111}In$, $^{124}I$, $^{125}I$, or $^{131}I$.
49. A pharmaceutical composition comprising a conjugate of Formula I (Formula I)

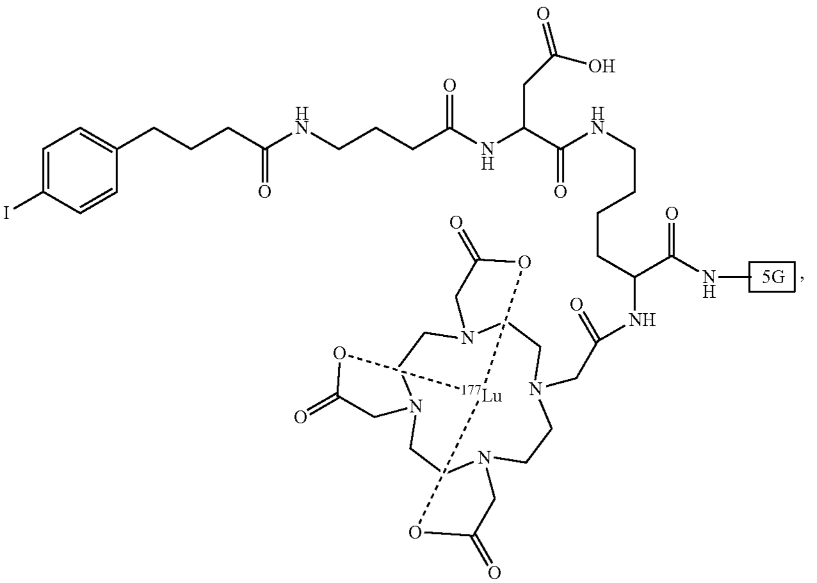

wherein 5G is a PEGylated peptide having the amino acid sequence GNGVPNLRGDLQVLGQRVGRT and comprising a first PEG moiety at the N-terminus of the peptide and a second PEG moiety at the C-terminus of the peptide; and a pharmaceutically acceptable excipient.

50. The pharmaceutical composition of embodiment 49, wherein the first PEG moiety and the second PEG moiety are the same.
51. The pharmaceutical composition of embodiment 49 or 50, wherein the first PEG moiety and the second PEG moiety each comprises PEG28 (PEG 1500).
52. The pharmaceutical composition of any one of embodiments 49-51, wherein the composition contains between about 25 mCi and about 200 mCi radioactivity.
53. A pharmaceutical composition comprising a conjugate of Formula II (Formula II)

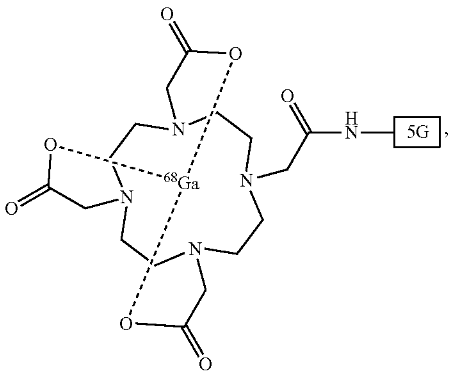

wherein 5G is a PEGylated peptide having the amino acid sequence GNGVPNLRGDLQVLGQRVGRT and comprising a first PEG moiety at the N-terminus of the peptide and a second PEG moiety at the C-terminus of the peptide; and a pharmaceutically acceptable excipient.
54. The pharmaceutical composition of embodiment 53, wherein the first PEG moiety and the second PEG moiety are the same.
55. The pharmaceutical composition of embodiment 53 or 54, wherein the first PEG moiety and the second PEG moiety each comprises PEG28 (PEG 1500).

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

What is claimed is:

1. A pharmaceutical composition comprising a peptide having the amino acid sequence GNGVPNLRGDLQVLGQRVGRT (SEQ ID NO.: 1).

2. The pharmaceutical composition of claim 1, wherein the peptide has an N-terminus and a C-terminus and a PEG moiety is covalently attached at the N-terminus, the C-terminus or both the N- and C-termini of the peptide.

3. The pharmaceutical composition of claim 1, wherein the peptide is covalently attached to an albumin binding moiety (ABM).

4. The pharmaceutical composition of claim 1, wherein the peptide is covalently attached to a chelating moiety.

5. The pharmaceutical composition of claim 4, wherein a radionuclide is complexed with the chelating moiety.

6. The pharmaceutical composition of claim 5, wherein the radionuclide is selected from the group consisting of an alpha emitter, a beta emitter, and a gamma emitter.

7. The pharmaceutical composition of claim 5, wherein the radionuclide is a positron emitter.

8. The pharmaceutical composition of claim 5, wherein the radionuclide is selected from the group consisting of $^{32}P$, $^{47}Sc$, $^{67}Cu$, $^{89}Sr$, $^{90}Y$, $^{105}Rh$, $^{111}Ag$, $^{117m}Sn$, $^{131}I$, $^{149}Pm$, $^{153}Sm$, $^{166}Ho$, $^{177}Lu$, $^{186}Re$, $^{188}Re$, $^{211}At$, $^{225}Ac$, $^{212}Bi$, $^{11}C$, $^{13}N$, $^{15}O$, $^{18}F$, $^{55}Co$, $^{60}Cu$, $^{61}Cu$, $^{62}Cu$, $^{64}Cu$, $^{66}Ga$, $^{67}Cu$, $^{68}Ga$, $^{82}Rb$, $^{86}Y$, $^{111}In$, $^{124}I$, $^{125}I$, and $^{131}I$.

9. The pharmaceutical composition of claim 1, further comprising a pharmaceutically acceptable excipient and wherein the peptide has an N-terminus and a C terminus, wherein a first PEG moiety is covalently attached to the N-terminus of the peptide and a second PEG moiety is covalently attached to the C-terminus of the peptide to provide a PEGylated peptide, and further wherein the PEGylated peptide is provided as a conjugate of Formula I (Formula I)

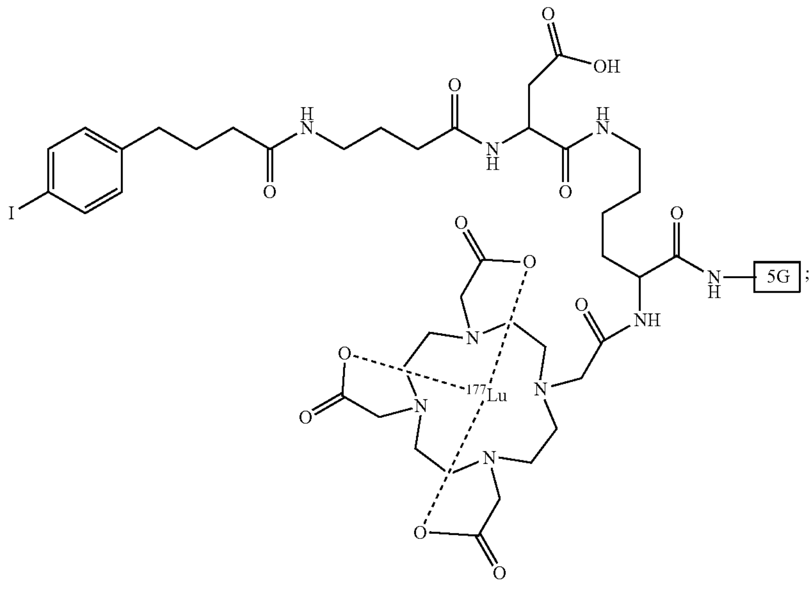

;

wherein 5G is the PEGylated peptide.

10. The pharmaceutical composition of claim 1, further comprising a pharmaceutically acceptable excipient and wherein the peptide has an N-terminus and a C terminus, wherein a first PEG moiety is covalently attached to the N-terminus of the peptide and a second PEG moiety is covalently attached to the C-terminus of the peptide to provide a PEGylated peptide, and further wherein the PEGylated peptide is provided as a conjugate of Formula II (Formula II)

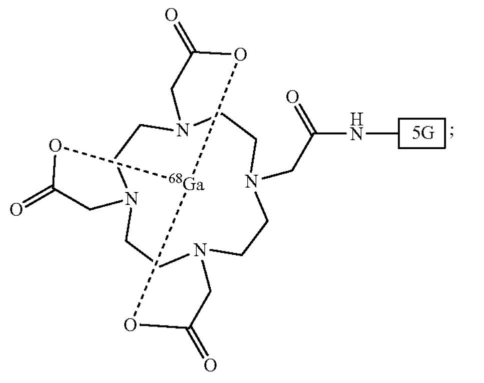

wherein 5G is the PEGylated peptide.

11. A method for treating an $\alpha_v\beta_6$ integrin-related cancer, the method comprising administering a dose of a therapeutic conjugate of Formula I to a subject in need of treatment 12. The method of claim 11, wherein the dose of the therapeutic conjugate contains between about 25 mCi and about 200 mCi radioactivity.

13. The method of claim 11, wherein the $\alpha_v\beta_6$ integrin-related cancer is selected from the group consisting of pancreatic cancer, breast cancer, colorectal cancer, lung cancer, ovarian cancer, cervical cancer, oral squamous cell carcinoma, skin squamous cell carcinoma, head and neck cancer, stomach cancer, and endometrial cancer.

14. The method of claim 13, wherein the $\alpha_v\beta_6$ integrin-related cancer comprises one or more metastases.

15. The method of claim 11, wherein the subject receives a standard of care treatment prior to and/or subsequent to the administering the therapeutic conjugate.

16. The method of claim 15 wherein the standard of care treatment comprises one or more of surgery, radiation therapy, chemotherapy, chemoradiation therapy and targeted therapy.

17. The method of claim 11, further comprising administering a diagnostic conjugate prior to the administration of the therapeutic conjugate, wherein the diagnostic conjugate comprises an RGD peptide and a second radionuclide.

(Formula I)

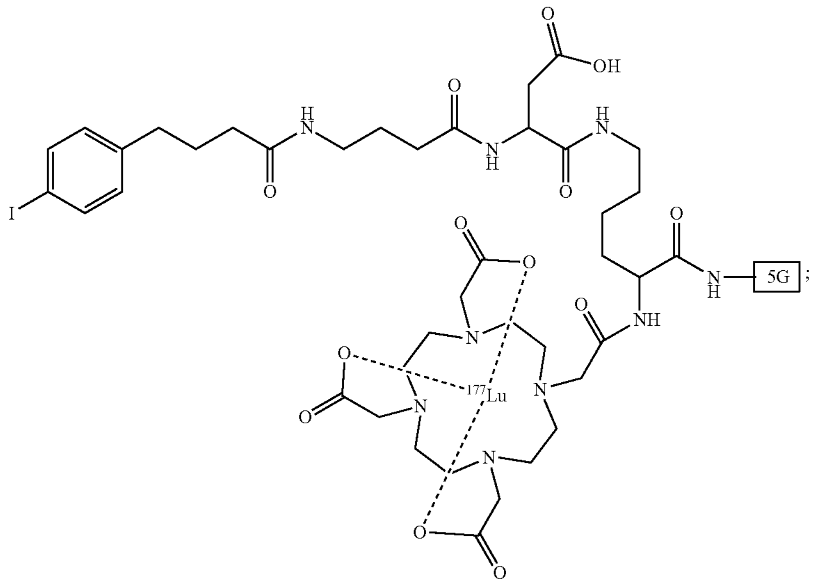

wherein 5G is a PEGylated peptide having an N-terminus, a C-terminus, and the amino acid sequence GNGVPNLRGDLQVLGQRVGRT (SEQ ID NO.: 1);

and wherein a first PEG moiety is covalently attached to the N-terminus of the peptide and a second PEG moiety is covalently attached to the C-terminus of the peptide.

18. The method of claim 17 wherein the second radionuclide is selected from the group consisting of $^{11}C$, $^{13}N$, $^{15}O$, $^{18}F$, $^{55}Co$, $^{60}Cu$, $^{61}Cu$, $^{62}Cu$, $^{64}Cu$, $^{66}Ga$, $^{67}Cu$, $^{68}Ga$, $^{82}Rb$, $^{86}Y$, $^{111}In$, $^{124}I$, $^{125}I$, or $^{131}I$.

19. The method of claim 17, wherein the diagnostic conjugate comprises Formula II (Formula II)

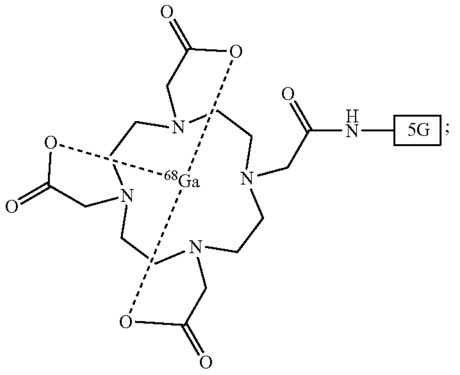

wherein 5G is a PEGylated peptide having an N-terminus, a C-terminus, and the amino acid sequence GNGVPNLRGDLQVLGQRVGRT (SEQ ID NO.: 1);

and wherein a first PEG moiety is covalently attached to the N-terminus of the peptide and a second PEG moiety is covalently attached to the C-terminus of the peptide.

20. A method for imaging a tumor, a cancerous lesion, or a cancer cell, the method comprising administering a diagnostic conjugate comprising Formula II and a pharmaceutically acceptable excipient to a subject (Formula II)

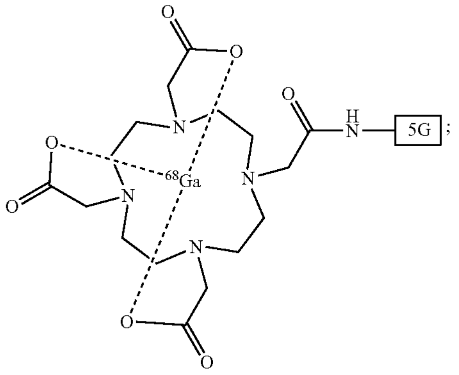

wherein 5G is a PEGylated peptide having a, N-terminus, a C-terminus, and the amino acid sequence GNGVPNLRGDLQVLGQRVGRT (SEQ ID NO.: 1);
and wherein a first PEG moiety is covalently attached to the N-terminus of the peptide and a second PEG moiety is covalently attached to the C-terminus of the peptide.

21. The method of claim 20, further comprising administering a therapeutic agent.

22. The method of claim 21, wherein the therapeutic agent comprises an RGD peptide.

* * * * *